US009918982B2

(12) United States Patent
Yum et al.

(10) Patent No.: US 9,918,982 B2
(45) Date of Patent: *Mar. 20, 2018

(54) ORAL DRUG DELIVERY SYSTEM

(71) Applicant: DURECT CORPORATION, Cupertino, CA (US)

(72) Inventors: Su Il Yum, Los Altos, CA (US); Grant Schoenhard, San Carlos, CA (US); Arthur J. Tipton, Birmingham, AL (US); John W. Gibson, Springville, AL (US); John C. Middleton, Fort Collins, CO (US); Roger Fu, Saratoga, CA (US); Michael S. Zamloot, Austin, TX (US)

(73) Assignee: Durect Corporation, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/342,956

(22) Filed: Nov. 3, 2016

(65) Prior Publication Data

US 2017/0165255 A1   Jun. 15, 2017

Related U.S. Application Data

(63) Continuation of application No. 14/957,148, filed on Dec. 2, 2015, now Pat. No. 9,517,271, which is a continuation of application No. 14/574,024, filed on Dec. 17, 2014, now Pat. No. 9,233,160, which is a continuation of application No. 13/786,118, filed on Mar. 5, 2013, now Pat. No. 8,945,614, which is a continuation of application No. 13/366,168, filed on Feb. 3, 2012, now Pat. No. 8,420,120, which is a continuation of application No. 10/737,144, filed on Dec. 15, 2003, now Pat. No. 8,133,507.

(60) Provisional application No. 60/517,464, filed on Nov. 4, 2003, provisional application No. 61/433,116, filed on Dec. 13, 2002.

(51) Int. Cl.

| A61K 31/485 | (2006.01) |
|---|---|
| A61K 47/38 | (2006.01) |
| A61K 9/00 | (2006.01) |
| A61K 9/48 | (2006.01) |
| A61K 47/26 | (2006.01) |
| A61K 47/14 | (2017.01) |
| A61K 31/4458 | (2006.01) |

(52) U.S. Cl.
CPC .......... *A61K 31/485* (2013.01); *A61K 9/0053* (2013.01); *A61K 9/48* (2013.01); *A61K 9/4825* (2013.01); *A61K 9/4858* (2013.01); *A61K 9/4866* (2013.01)

(58) Field of Classification Search
CPC .. A61K 47/38; A61K 31/485; A61K 31/4458; A61K 47/26; A61K 47/14; A61K 9/0053; A61K 9/48; A61K 9/4858; A61K 9/4866
See application file for complete search history.

(56) References Cited

U.S. PATENT DOCUMENTS

| 2,799,241 A | 7/1957 | Wurster |
|---|---|---|
| 2,931,802 A | 4/1960 | Toney et al. |
| 3,339,546 A | 9/1967 | Chen |
| 3,743,398 A | 7/1973 | Johnson et al. |
| 3,845,770 A | 11/1974 | Theeuwes et al. |
| 3,853,837 A | 12/1974 | Fujino et al. |
| 3,916,889 A | 11/1975 | Russell |
| 3,916,899 A | 11/1975 | Theeuwes et al. |
| 3,952,741 A | 4/1976 | Baker |
| 3,992,365 A | 11/1976 | Beddell et al. |
| 3,995,631 A | 12/1976 | Higuchi et al. |
| 4,008,719 A | 2/1977 | Theeuwes et al. |
| 4,014,334 A | 3/1977 | Theeuwes et al. |
| 4,016,880 A | 4/1977 | Theeuwes et al. |
| 4,024,248 A | 5/1977 | Konig et al. |
| 4,063,064 A | 12/1977 | Saunders et al. |
| 4,088,864 A | 5/1978 | Theeuwes et al. |
| 4,100,274 A | 7/1978 | Dutta et al. |
| 4,111,202 A | 9/1978 | Theeuwes |
| 4,160,020 A | 7/1979 | Ayer et al. |
| 4,327,725 A | 5/1982 | Cortese et al. |
| 4,360,019 A | 11/1982 | Portner et al. |
| 4,395,405 A | 7/1983 | Noda et al. |
| 4,395,495 A | 7/1983 | Cummings |
| 4,411,890 A | 10/1983 | Momany |
| 4,487,603 A | 12/1984 | Harris |
| 4,530,840 A | 7/1985 | Tice et al. |
| 4,578,075 A | 3/1986 | Urquhart et al. |
| 4,622,219 A | 11/1986 | Haynes |
| 4,681,583 A | 7/1987 | Urquhart et al. |

(Continued)

FOREIGN PATENT DOCUMENTS

| AU | 8374575 | 8/1975 |
|---|---|---|
| CA | 2222567 | 1/2002 |

(Continued)

OTHER PUBLICATIONS

U.S. Appl. No. 15/380,828, filed Dec. 15, 2016, Yum, et al.
U.S. Appl. No. 15/398,426, filed Jan. 4, 2017, Yum, et al.
"New Drugs/Programs"; *Current Drug Discovery*; Nov. 2004; pp. 7-10.
"Ritalin product monograph"; *CPS Compendium of Pharmaceuticals and Specialties*, 34th ed.; Gillis, M., Ed. Canadian Pharmacists Association: Ottawa, (1999); pp. 1573-1574.
3M, "3M DDS Announces Development of New HFA-Compatible Exipients: Novel Oligomeric Acids as MDI Suspension Aid and Solubilizers" *3M Delivery Newsletter*, vol. 15, 3M Drug Delivery Systems; Jun. 2000, pp. 9-11.
Abdul-Fattah, Ahmad M., et al; "Preparation and In Vitro Evaluation of Solid Dispersions of Halofantrine."; *International Journal of Pharmaceutics 235*; (2002); pp. 17-33.
Adams, Edgar G, et al.; "A comparison of the abuse liability of tramadol, NSAIDS, and hydrocodone in patients with chronic pain"; *Journal of Pain and Symptom Management.* 31(5); (2006); pp. 465-476.

(Continued)

*Primary Examiner* — Blessing M Fubara
(74) *Attorney, Agent, or Firm* — Carol L. Francis; Bozicevic, Field & Francis LLP

(57) ABSTRACT

Dosage forms and drug delivery devices suitable for administration of pharmaceutical compounds and compositions, including the oral drug administration of compounds.

21 Claims, 11 Drawing Sheets

(56) References Cited

U.S. PATENT DOCUMENTS

| | | |
|---|---|---|
| 4,681,765 A | 7/1987 | Guley |
| 4,689,222 A * | 8/1987 | McMichael .......... A61K 35/744 |
| | | 424/115 |
| 4,692,147 A | 9/1987 | Duggan |
| 4,725,442 A | 2/1988 | Haynes |
| 4,725,852 A | 2/1988 | Gamblin et al. |
| 4,767,628 A | 8/1988 | Hutchinson |
| 4,769,372 A | 9/1988 | Kreek |
| 4,795,641 A | 1/1989 | Kashdan |
| 4,834,984 A | 5/1989 | Goldie et al. |
| 4,844,909 A | 7/1989 | Goldie et al. |
| 4,861,598 A | 8/1989 | Oshlack |
| 4,891,225 A | 1/1990 | Langer et al. |
| 4,906,474 A | 3/1990 | Langer et al. |
| 4,931,285 A | 6/1990 | Edgren et al. |
| 4,938,763 A | 7/1990 | Dunn et al. |
| 4,957,681 A | 9/1990 | Klimesch et al. |
| 4,957,744 A | 9/1990 | della Valle et al. |
| 4,961,932 A | 10/1990 | Theeuwes |
| 4,970,075 A | 11/1990 | Oshlack |
| 4,990,341 A | 2/1991 | Goldie et al. |
| 5,006,346 A | 4/1991 | Edgren et al. |
| 5,019,397 A | 5/1991 | Wong et al. |
| 5,024,842 A | 6/1991 | Edgren et al. |
| 5,149,543 A | 9/1992 | Cohen et al. |
| 5,156,850 A | 10/1992 | Wong et al. |
| 5,160,743 A | 11/1992 | Edgren et al. |
| 5,188,837 A | 2/1993 | Domb |
| 5,190,765 A | 3/1993 | Jao et al. |
| 5,252,338 A | 10/1993 | Jao et al. |
| 5,266,331 A | 11/1993 | Oshlack et al. |
| 5,273,760 A | 12/1993 | Oshlack et al. |
| 5,278,201 A | 1/1994 | Dunn et al. |
| 5,278,202 A | 1/1994 | Dunn et al. |
| 5,286,493 A | 2/1994 | Oshlack et al. |
| 5,286,496 A | 2/1994 | Stapler et al. |
| 5,324,351 A | 6/1994 | Oshlack et al. |
| 5,324,519 A | 6/1994 | Dunn et al. |
| 5,324,520 A | 6/1994 | Dunn et al. |
| 5,330,835 A | 7/1994 | Kikuchi et al. |
| 5,340,572 A | 8/1994 | Patel et al. |
| 5,340,849 A | 8/1994 | Dunn et al. |
| 5,350,741 A | 9/1994 | Takada |
| 5,352,662 A | 10/1994 | Brooks et al. |
| 5,356,467 A | 10/1994 | Oshlack et al. |
| 5,356,635 A | 10/1994 | Raman et al. |
| 5,366,738 A | 11/1994 | Rork et al. |
| 5,382,424 A | 1/1995 | Stapler et al. |
| 5,391,381 A | 2/1995 | Wong et al. |
| 5,399,363 A | 3/1995 | Liversidge et al. |
| 5,472,712 A | 12/1995 | Oshlack et al. |
| 5,478,577 A | 12/1995 | Sackler et al. |
| 5,487,898 A | 1/1996 | Lu et al. |
| 5,508,042 A | 4/1996 | Oshlack et al. |
| 5,540,912 A | 7/1996 | Roorda et al. |
| 5,545,408 A | 8/1996 | Trigg et al. |
| 5,549,912 A | 8/1996 | Oshlack et al. |
| 5,569,450 A | 10/1996 | Duan et al. |
| 5,580,578 A | 12/1996 | Oshlack et al. |
| 5,599,552 A | 2/1997 | Dunn et al. |
| 5,620,705 A | 4/1997 | Dong et al. |
| 5,633,000 A | 5/1997 | Grossman et al. |
| 5,633,011 A | 5/1997 | Dong et al. |
| 5,639,476 A | 6/1997 | Oshlack et al. |
| 5,656,295 A | 8/1997 | Oshlack et al. |
| 5,672,360 A | 9/1997 | Sackler et al. |
| 5,681,585 A | 10/1997 | Oshlack et al. |
| 5,702,716 A | 12/1997 | Dunn et al. |
| 5,725,841 A | 3/1998 | Duan et al. |
| 5,728,396 A | 3/1998 | Peery et al. |
| 5,733,950 A | 3/1998 | Dunn et al. |
| 5,736,152 A | 4/1998 | Dunn |
| 5,739,176 A | 4/1998 | Dunn et al. |
| 5,744,280 A * | 4/1998 | Mooney, III ............ C09B 11/04 |
| | | 430/270.1 |
| 5,747,051 A | 5/1998 | Granger et al. |
| 5,747,058 A * | 5/1998 | Tipton ..................... A61K 8/60 |
| | | 424/423 |
| 5,750,100 A | 5/1998 | Yamagata et al. |
| 5,759,563 A | 6/1998 | Yewey et al. |
| 5,777,124 A | 7/1998 | Zavareh et al. |
| 5,780,044 A | 7/1998 | Yewey et al. |
| 5,786,484 A | 7/1998 | Dyer et al. |
| 5,837,284 A | 11/1998 | Mehta et al. |
| 5,840,329 A | 11/1998 | Bai |
| 5,840,731 A | 11/1998 | Mayer et al. |
| 5,879,705 A | 3/1999 | Haefield et al. |
| 5,908,850 A | 6/1999 | Zeitlin et al. |
| 5,919,473 A | 7/1999 | Elkhoury |
| 5,932,597 A | 8/1999 | Brown |
| 5,942,241 A | 8/1999 | Chasin et al. |
| 5,958,446 A | 9/1999 | Miranda et al. |
| 5,958,452 A | 9/1999 | Oshlack et al. |
| 5,965,161 A | 10/1999 | Oshlack et al. |
| 5,968,542 A | 10/1999 | Tipton |
| 5,985,305 A | 11/1999 | Peery et al. |
| 5,994,548 A | 11/1999 | Langston et al. |
| 6,008,355 A | 12/1999 | Huang et al. |
| 6,042,811 A | 3/2000 | Duan et al. |
| 6,051,558 A | 4/2000 | Burns et al. |
| 6,093,419 A | 7/2000 | Rolf |
| 6,126,919 A | 10/2000 | Stefely et al. |
| 6,143,322 A | 11/2000 | Sackler et al. |
| 6,190,680 B1 | 2/2001 | Sakurada et al. |
| 6,203,813 B1 | 3/2001 | Gooberman et al. |
| 6,210,705 B1 | 4/2001 | Mantelle et al. |
| 6,228,398 B1 | 5/2001 | Devane et al. |
| 6,245,351 B1 | 6/2001 | Nara et al. |
| 6,291,013 B1 | 9/2001 | Gibson et al. |
| 6,294,195 B1 | 9/2001 | Oshlack |
| 6,312,717 B1 | 11/2001 | Molinoff et al. |
| 6,344,215 B1 | 2/2002 | Bettman et al. |
| 6,348,211 B1 | 2/2002 | Mantelle et al. |
| 6,355,656 B1 | 3/2002 | Zeitlin et al. |
| 6,375,957 B1 | 4/2002 | Kaiko et al. |
| 6,384,227 B2 | 5/2002 | Dyer et al. |
| 6,403,609 B1 | 6/2002 | Asgharian et al. |
| 6,413,356 B1 | 7/2002 | Chokshi et al. |
| 6,413,536 B1 | 7/2002 | Gibson et al. |
| 6,419,960 B1 | 7/2002 | Krishnamurthy |
| 6,426,339 B1 | 7/2002 | Berde et al. |
| 6,440,493 B1 | 8/2002 | Gibson et al. |
| 6,479,074 B2 | 11/2002 | Murdock et al. |
| 6,486,138 B1 | 11/2002 | Asgharian et al. |
| 6,498,153 B1 | 12/2002 | Cady et al. |
| 6,512,009 B1 | 1/2003 | Daoust et al. |
| 6,514,516 B1 | 2/2003 | Chasin et al. |
| 6,521,259 B1 | 2/2003 | Chasin et al. |
| 6,524,607 B1 | 2/2003 | Goldenheim et al. |
| 6,528,530 B2 | 3/2003 | Zeitlin et al. |
| 6,552,031 B1 | 4/2003 | Burch et al. |
| 6,635,284 B2 | 10/2003 | Mehta et al. |
| 6,699,908 B2 | 3/2004 | Sackler et al. |
| 6,730,325 B2 | 5/2004 | Devane et al. |
| 6,733,783 B2 | 5/2004 | Oshlack et al. |
| 6,919,373 B1 | 7/2005 | Lam et al. |
| 6,921,541 B2 | 7/2005 | Chasin et al. |
| 6,930,129 B2 | 8/2005 | Lam et al. |
| 6,992,065 B2 | 1/2006 | Okumu et al. |
| 7,053,209 B1 | 5/2006 | Gibson et al. |
| 7,431,944 B2 | 10/2008 | Mehta et al. |
| 7,691,880 B2 | 4/2010 | Herman |
| 7,833,543 B2 * | 11/2010 | Gibson ..................... A61K 8/60 |
| | | 424/409 |
| 7,838,522 B2 | 11/2010 | Esposito et al. |
| 8,124,123 B2 | 2/2012 | Pillai et al. |
| 8,133,507 B2 * | 3/2012 | Yum ..................... A61K 9/4858 |
| | | 424/456 |
| 8,147,870 B2 * | 4/2012 | Yum ..................... A61K 9/4858 |
| | | 424/456 |
| 8,153,152 B2 * | 4/2012 | Yum ..................... A61K 9/4858 |
| | | 424/456 |
| 8,163,798 B2 | 4/2012 | Gupta et al. |

(56) References Cited

U.S. PATENT DOCUMENTS

| | | | | |
|---|---|---|---|---|
| 8,168,217 B2* | 5/2012 | Yum | .................... | A61K 9/4858 424/456 |
| 8,354,124 B2* | 1/2013 | Yum | .................... | A61K 9/4858 424/485 |
| 8,415,401 B2* | 4/2013 | Yum | .................... | A61K 9/4858 514/183 |
| 8,420,120 B2* | 4/2013 | Yum | .................... | A61K 9/4858 424/456 |
| 8,926,783 B2* | 1/2015 | Akhtar | .................... | C09D 5/008 156/247 |
| 8,945,614 B2* | 2/2015 | Yum | .................... | A61K 9/4858 424/456 |
| 8,951,556 B2* | 2/2015 | Yum | .................... | A61K 9/4858 424/456 |
| 8,974,821 B2* | 3/2015 | Yum | .................... | A61K 9/4858 424/456 |
| 9,233,160 B2* | 1/2016 | Yum | .................... | A61K 9/4858 |
| 9,517,271 B2* | 12/2016 | Yum | .................... | A61K 9/4858 |
| 9,555,113 B2* | 1/2017 | Yum | .................... | A61K 31/485 |
| 9,572,885 B2* | 2/2017 | Yum | .................... | A61K 31/485 |
| 9,592,204 B2 | 3/2017 | Yum et al. | | |
| 9,616,055 B2 | 4/2017 | Scicinski et al. | | |
| 9,655,861 B2* | 5/2017 | Yum | .................... | A61K 9/4866 |
| 2001/0000522 A1 | 4/2001 | Dyer et al. | | |
| 2001/0029257 A1 | 10/2001 | Murdock et al. | | |
| 2001/0047005 A1 | 11/2001 | Farrar et al. | | |
| 2001/0055613 A1 | 12/2001 | Burnside et al. | | |
| 2002/0086878 A1 | 7/2002 | Dobrozsi et al. | | |
| 2002/0114835 A1 | 8/2002 | Sackler et al. | | |
| 2002/0143065 A1 | 10/2002 | Liu et al. | | |
| 2003/0004177 A1 | 1/2003 | Kao et al. | | |
| 2003/0045454 A1 | 3/2003 | Okumu et al. | | |
| 2003/0152637 A1 | 8/2003 | Chasin et al. | | |
| 2003/0157168 A1 | 8/2003 | Breder et al. | | |
| 2003/0165562 A1 | 9/2003 | Gutierrez-Rocca et al. | | |
| 2003/0185873 A1 | 10/2003 | Chasin et al. | | |
| 2003/0191147 A1 | 10/2003 | Sherman et al. | | |
| 2004/0001889 A1 | 1/2004 | Chen et al. | | |
| 2004/0024021 A1 | 2/2004 | Sudo et al. | | |
| 2004/0052336 A1 | 3/2004 | Langlet et al. | | |
| 2004/0101557 A1 | 5/2004 | Gibson et al. | | |
| 2004/0109893 A1 | 6/2004 | Chen et al. | | |
| 2004/0138237 A1 | 7/2004 | Shah | | |
| 2004/0146562 A1 | 7/2004 | Shah | | |
| 2004/0224020 A1 | 11/2004 | Schoenhard | | |
| 2004/0224903 A1 | 11/2004 | Berry et al. | | |
| 2005/0042194 A1 | 2/2005 | Ng et al. | | |
| 2005/0106304 A1 | 5/2005 | Cook et al. | | |
| 2005/0158382 A1 | 7/2005 | Cruz et al. | | |
| 2005/0171052 A1 | 8/2005 | Cook et al. | | |
| 2005/0208132 A1 | 9/2005 | Sathyan et al. | | |
| 2005/0232876 A1 | 10/2005 | Minga et al. | | |
| 2005/0244489 A1 | 11/2005 | Paris | | |
| 2005/0260264 A1 | 11/2005 | Edgren et al. | | |
| 2005/0266087 A1 | 12/2005 | Junnarkar et al. | | |
| 2006/0034926 A1 | 2/2006 | Fraatz et al. | | |
| 2006/0058401 A1 | 3/2006 | Ishikawa et al. | | |
| 2006/0104909 A1 | 5/2006 | Vaghefi et al. | | |
| 2006/0115527 A1 | 6/2006 | Hassan et al. | | |
| 2006/0165800 A1 | 7/2006 | Chen et al. | | |
| 2006/0210599 A1 | 9/2006 | Gibson et al. | | |
| 2007/0027105 A1 | 2/2007 | Junnarkar et al. | | |
| 2007/0031502 A1 | 2/2007 | Pettersson et al. | | |
| 2007/0104763 A1 | 5/2007 | Jobdevairakkam et al. | | |
| 2007/0259033 A1 | 11/2007 | Cruz | | |
| 2008/0023261 A1 | 1/2008 | Kaneko et al. | | |
| 2008/0026052 A1 | 1/2008 | Schoenhard | | |
| 2008/0145419 A1 | 6/2008 | Gibson et al. | | |
| 2008/0152708 A1 | 6/2008 | Gibson et al. | | |
| 2008/0206321 A1 | 8/2008 | Yum et al. | | |
| 2009/0023689 A1 | 1/2009 | Yum et al. | | |
| 2009/0023690 A1 | 1/2009 | Yum et al. | | |
| 2009/0164240 A1 | 6/2009 | Friedmann et al. | | |
| 2009/0165578 A1 | 7/2009 | Zamloot et al. | | |
| 2009/0169631 A1 | 7/2009 | Zamloot et al. | | |
| 2009/0215808 A1 | 8/2009 | Yum et al. | | |
| 2009/0298862 A1 | 12/2009 | Yum et al. | | |
| 2010/0260844 A1 | 10/2010 | Scicinski et al. | | |
| 2011/0287093 A1 | 11/2011 | Schoenhard | | |
| 2012/0135072 A1 | 5/2012 | Yum et al. | | |
| 2012/0135073 A1 | 5/2012 | Yum et al. | | |
| 2012/0165358 A1 | 6/2012 | Cruz et al. | | |
| 2013/0281480 A1 | 10/2013 | Yum et al. | | |
| 2013/0287845 A1 | 10/2013 | Yum et al. | | |
| 2013/0295168 A1 | 11/2013 | Yum et al. | | |
| 2013/0309176 A1 | 11/2013 | Port et al. | | |
| 2013/0317049 A1 | 11/2013 | Yum et al. | | |
| 2013/0337059 A1 | 12/2013 | Yum et al. | | |
| 2013/0337060 A1 | 12/2013 | Yum et al. | | |
| 2014/0275147 A1 | 3/2014 | Yum et al. | | |
| 2015/0196644 A1 | 7/2015 | Yum et al. | | |
| 2016/0038592 A1 | 2/2016 | Yum et al. | | |
| 2016/0136102 A1 | 5/2016 | Yum et al. | | |
| 2016/0193345 A1 | 7/2016 | Yum et al. | | |
| 2016/0038479 A1 | 9/2016 | Yum et al. | | |

FOREIGN PATENT DOCUMENTS

| | | |
|---|---|---|
| DE | 1569231 | 8/1969 |
| DE | 2213717 | 11/1972 |
| DE | 2321174 | 4/1973 |
| DE | 2438352 | 2/1976 |
| DE | 2720245 | 11/1977 |
| DE | 19714765 | 10/1998 |
| EP | 0244118 | 11/1987 |
| EP | 0535899 | 4/1993 |
| EP | 0539559 | 5/1993 |
| EP | 0539751 | 5/1993 |
| EP | 0544612 | 6/1993 |
| EP | 0621042 | 10/1994 |
| EP | 0290983 | 1/1995 |
| EP | 0635531 | 2/1995 |
| EP | 0640336 | 3/1995 |
| EP | 0711548 | 5/1996 |
| EP | 0773034 | 5/1997 |
| EP | 0778768 | 6/1997 |
| EP | 0537559 | 1/1998 |
| EP | 1010436 | 6/2000 |
| EP | 0782569 | 3/2002 |
| EP | 0804417 | 6/2003 |
| EP | 0788480 | 7/2003 |
| EP | 0788481 | 8/2003 |
| EP | 0999825 | 10/2003 |
| EP | 1348427 | 10/2003 |
| EP | 1032390 | 11/2003 |
| EP | 1548093 | 6/2005 |
| EP | 2510924 | 10/2012 |
| GB | 1088992 | 10/1967 |
| GB | 2238478 | 6/1991 |
| JP | 59210024 | 11/1984 |
| JP | 62000419 | 1/1987 |
| JP | 2096516 | 4/1990 |
| JP | 5194273 | 8/1993 |
| JP | 7053356 | 2/1995 |
| JP | 7112940 | 5/1995 |
| JP | 7115901 | 5/1995 |
| JP | 7124196 | 5/1995 |
| JP | 9502181 | 3/1997 |
| JP | 2003508449 | 3/2003 |
| WO | WO 1990003768 | 4/1990 |
| WO | WO 1990003809 | 4/1990 |
| WO | WO 1991018016 | 11/1991 |
| WO | WO 1992014466 | 3/1992 |
| WO | WO 1992017900 | 10/1992 |
| WO | WO 1993003751 | 3/1993 |
| WO | WO 1993007833 | 4/1993 |
| WO | WO 1994005265 | 3/1994 |
| WO | WO 1994015587 | 7/1994 |
| WO | WO 1995009613 | 4/1995 |
| WO | WO 1995017901 | 7/1995 |
| WO | WO 1996009290 | 3/1996 |
| WO | WO 1996012699 | 5/1996 |
| WO | WO 1996012700 | 5/1996 |

(56) References Cited

FOREIGN PATENT DOCUMENTS

| WO | WO 1996022281 | 7/1996 |
|---|---|---|
| WO | 1996039995 | 12/1996 |
| WO | WO 1996041616 | 12/1996 |
| WO | WO 1997015285 | 5/1997 |
| WO | WO 1997027840 | 8/1997 |
| WO | WO 1997049391 | 12/1997 |
| WO | WO 1998027962 | 7/1998 |
| WO | WO 1998027963 | 7/1998 |
| WO | WO 1998034596 | 8/1998 |
| WO | WO 1998044903 | 10/1998 |
| WO | WO 1998051246 | 11/1998 |
| WO | WO 1998053837 | 12/1998 |
| WO | WO 1999006023 | 2/1999 |
| WO | 1999013913 | 3/1999 |
| WO | WO 1999025349 | 5/1999 |
| WO | WO 2000000120 | 1/2000 |
| WO | WO 2000016750 | 3/2000 |
| WO | WO 2000078335 | 12/2000 |
| WO | WO 2001008661 | 2/2001 |
| WO | WO 2001015734 | 3/2001 |
| WO | WO 2001051024 | 7/2001 |
| WO | WO 2001076599 | 10/2001 |
| WO | WO 2002010436 | 2/2002 |
| WO | WO 2002053187 | 7/2002 |
| WO | WO 2002087512 | 11/2002 |
| WO | WO 2003000282 | 1/2003 |
| WO | WO 2003013476 | 2/2003 |
| WO | WO 2003055475 | 7/2003 |
| WO | WO 2003086368 | 10/2003 |
| WO | WO 2003101358 | 12/2003 |
| WO | WO 2004026262 | 4/2004 |
| WO | WO 2004037224 | 5/2004 |
| WO | WO 2004037289 | 5/2004 |
| WO | WO 2004052336 | 6/2004 |
| WO | WO 2004054542 | 7/2004 |
| WO | WO 2004056337 | 7/2004 |
| WO | WO 2004056338 | 7/2004 |
| WO | WO 2004082658 | 9/2004 |
| WO | WO 2004101557 | 11/2004 |
| WO | WO 2005009408 | 2/2005 |
| WO | WO 2005048744 | 6/2005 |
| WO | WO 2005105031 | 11/2005 |
| WO | WO 2005112896 | 12/2005 |
| WO | WO 2005115333 | 12/2005 |
| WO | WO 2006008141 | 1/2006 |
| WO | WO 2006069293 | 6/2006 |
| WO | WO 2006084139 | 8/2006 |
| WO | WO 2007058923 | 5/2007 |
| WO | WO 2008023261 | 2/2008 |
| WO | WO 2009076227 | 6/2009 |
| WO | WO 2009076231 | 6/2009 |
| WO | WO 2009076236 | 6/2009 |
| WO | WO 2013142279 | 9/2013 |
| WO | WO 2014144984 | 3/2014 |
| WO | WO 2014144975 | 9/2014 |

OTHER PUBLICATIONS

Ajayaghosh, A., et al., "Solid-Phase Synthesis of N-Methyl- and N-Ethylamides of Peptides Using Photolytically Detachable ((3-Nitro-4-((alkylamino)methyl)benzamido)methyl)polystyrene Resin"; *J. Org. Chem.* 55; (1990); pp. 2826-2829.

Allahham Allahham, et al; "Flow and injection characteristics of pharmaceutical parenteral formulations using a micro-capillary rheometer"; *International Journal of Pharmaceutics.* 270; (2004); pp. 139-148.

Ansel, H.C. et al.; *Pharmaceutical Dosage Forms and Drug Delivery System,* sixth ed., (1995); 20 pages.

Ash Michael and Ash Irene; "Handbook of Pharmaceutical Additives: An International Guide to More Than 6000 Products by Trade Name, Chemical, Function, and Manufacturer" ; *Gower* (1995); 3 pages.

Aungst, B.J., et al; "Improved Oral Bioavailability of an HIV Protease Inhibitor Using Gelucire 44/14 and Labrasol Vehicles"; *Bulletin Technique Gattefosse,* No. 87; (1994); pp. 49-54.

Aungst, B.J., et al; "Amphiphilic vehicles improve the oral bioavailability of a poorly soluble HIV Protease inhibitor at high doses."; *International Journal of Pharmaceutics,* vol. 156; (1997); pp. 79-88.

Bansal, Tripta, et al; "Solid Self Nanoemulsifying Delivery Systems as a Platform Technology for Formulation of Poorly Soluble Drugs"; *Critical Reviews™ in Therapeutic Drug Carrier Systems,* 25(1); (2008); pp. 63-116.

Barakat, N.S.; "Etodolac-Liquid-Filled Dispersion into Hard Gelatin Capsules: An Approach to Improve Dissolution and Stability of Etodolac Formulation"; *Drug Development and Indistrial Pharmacy.* 32; (2006); pp. 865-876.

Barb, R., et al.; "Evaluation of the SABER Delivery System for the Controlled Release of Deslorelin: Effect of Dose in Estrogen Primed Ovarectomized Gilts"; *Proceed Int'l, Symp. Control. Rel. Bioact. Mater.;* (1999) Controlled Release Society, Inc.; pp. 1170-1171.

Barker, S.A., et al; "An investigation into the structure and bioavailability of αtocopherol dispersions in Gelucire 44/14"; *Journal of Controlled Release 91;* (2003); pp. 477-488.

Becker & Johnson "Effects of Gonadotropin-Releasing Hormone Infused in a Pulsatile or Continuous Fashion Serum Gonadotropin Concentrations and Ovulation in the Mare"; *J. Anim. Sci.* vol. 70; (1992);. pp. 1208-1215.

Bekersky I, et al.; "Effect of low- and high-fat meals on tacrolimus absorption following 5 mg single oral doses to healthy human subjects"; *J Clin Pharmacol;* 41; (2001); pp. 176-182.

Berge et al. "Pharmaceutical salts" *J Pharm. Sci.* 66(1); Jan. 1977; pp. 1-19.

Betschart, R., et al.; "Evaluation of the SABER™ Delivery System for the Controlled Release of the GnRH Analogue Deslorelin for Advancing Ovulation in Mares: Effect of Gamma Radiation"; *Proceed. Int'l. Symp. Control. Rel. Bioact. Mater., 25, Controlled Release Society Inc.;* (1998); pp. 655-656.

Blachez, P., et al; "Development of immediate release pellets of poorly soluble compounds using Gelucire® 44/14 using melt pelletization"; Poster, Conference *"AAPS Annual Meeting & Exposition";* Salt Lake City, Utah, United States; Oct. 26, 2003; 2 pages.

Blažková, A. et al; "Viscosity properties of aqueous solutions of hydroxyethylcellulose"; *Chem Papers* 44(3); (1990); pp. 289-301.

Brevard J, et al. "Pain and opioid abuse in a population of substance abuse patients: data from the NAVIPPRO™ system." *Conference paper presented at the 42nd American Pain Society (APS) Annual Scientific Meeting,* Washington D.C.; (2007); 1 page.

Bühler, K.; GnRH Agonists and Safety, In GnRH Analagoues the State of the Art 1993, A Summary of the 3rd International Symposium on GnRH Analogues in Cancer and Human Reproduction, Geneva, Feb. 1993; pp. 139-146.

Burns, P. et al.; "Pharmacodynamic Evaluation of the Saber™ Delivery System for the Controlled Release of the GnRH Analogue Deslorelin Acetate for Advancing Ovulation in Cyclic Mares"; *Proceed. Int'l. Symp. Control. Rel. Bioact. Mater., 24; Controlled Release Society, Inc.* (1997); 4 pages.

"CAB-O-SIL®, Untreated Fumed Silica: Properties & Functions"; Cabot Corporation, Cab-O-Sil Division; (1993); pp. 1-34.

Carraway, et al.; "Drug Delivery From a Controlled Release Aerosol: Effects of Formulation Variables"; *AAPS J Abstract. Southern BioSystems, Inc.,* Birmingham AL, USA; (2000); 1 page.

Carraway, et al.; "Drug Release from a Novel Controlled Release Aerosol Based on Sucrose Acetate Isobutyrate" *AAPS Midwest Regional Meeting Chicago, IL;* May 22, 2000; 2 pages.

Cellulose Acetate Butyrate. In: European pharmacopoeia. 4 edn. Strasbourg Cedex, France: Council of Europe; (2001); pp. 853-854.

Chambin, O.; et al; "Interest of Multifunctional Lipid Excipients: Case of Gelucire® 44/14"; *Drug Development and Industrial Pharmacy,* 31; (2005); pp. 527-534.

Chambin, O., et al; "Influence of drug polarity upon the solid-state structure and release properties of self-emulsifying drug delivery systems in relation with water affinity"; *Colloids and Surfaces B: Biointerfaces 71;* (2009); pp. 73-78.

Chauhan, Bhaskar, et al; "Preparation and Characterization of Etoricoxib Solid Dispersions Using Lipid Carriers by Spray Drying Technique"; *AAPS PharmSciTech* 6(3), Article 50; (http://www.aapsphamscitech.org); (2005); pp. E405-E412.

(56) References Cited

OTHER PUBLICATIONS

Chauhan, B., et al; "Preparation and evaluation of glibenclamide-polyglycolized glycerides solid dispersions with silicon dioxide by spray drying technique"; *European J. Pharm. Sci.* 26(2); (2005); pp. 219-230.
Chen, X. Q., et al; "Evaluation of Lipid-Based Formulations in Dogs and Monkeys for a Highly Lipophilic Compound"; Conference "*Annual Meeting of AAPS*"; (2007); San Diego, CA; poster abstract; 1 page.
Coy, et al.; "Solid Phase Synthesis of Lutenizing Hormone-Releasing Hormone and Its Analogs"; *Methods Enzymol. 37;* (1975); pp. 416-424.
Cuine, Jean F., et al; "Evaluation of the Impact of Surfactant Digestion on the Bioavailability of Danazol after Oral Administration of Lipidic Self-Emulsifying Formulations to Dogs"; *Journal of Pharmaceutical Sciences,* vol. 97 No. 2; Feb. 2008; pp. 995-1012; article first published online Dec. 6, 2007.
Damian, Festo, et al; "Physicochemical characterization of solid dispersions of the antiviral agent UC-781 with polyethylene glycol 6000 and Gelucire 44/14"; *European Journal of Pharmaceutical Sciences 10;* (2000); pp. 311-322.
Darling, et al. (2000) "Extended Release of Human Growth Hormone Suspended in SABER™ Formulation Design and in Vitro Assessment" Genentech, Inc., South San Francisco, CA USA and Southern BioSystems, Inc. Birmingham AL, USA. Poster; 1 page.
DataBase WPI Section Ch, Week 198532 Derwent Publications Ltd., London GB; AN 1985-193549 XP002284488 & JP 60120811 A (Sealer, R P KK) Jun. 28, 1985 (Abstract).
Desai et al.; "Surface Modification of Polymeric Biomaterials for Reduced Thrombogenicity"; *Polym. Mater. Sci. Eng.,* 62; Jun. 1990;. pp. 731-735.
Dodson, K.M., et al. "Oral Controlled Release of Antiretrovirals Using the SABER Delivery System Incorporated into Soft Gelatin Capsules", *AAPS Meeting,* (1999), New Orleans, LA.; 2 pages.
Dordunoo, S.K., et al; "Preformulation Studies on Solid Dispersions Containing Triamterene or Temazepam in Polyethylene Glycols or Gelucire 44/14 for Liquid Filling of Hard Gelatin Capsules"; *Drug Development and Industrial Pharmacy,* vol. 17, No. 12; (1991); pp. 1685-1713.
Dordunoo, Stephen K., et al; "Solidification studies of polyethylene glycols, Gelucire® 44/14 or their dispersions with Triamterene or Temazepam"; *Journal of Pharm. Pharmacology 48;* (1996); pp. 782-789.
Duan, D.C. et al.; "Novel Dispersing Aids for Hydrofluoroalkane-Based Metered Dose Inhalers"; *1998 Conference of the American Association of Pharmaceutical Scientists,* San Francisco, California; Nov. 1998; 1 page.
Duan, D.C. et al., "Oligomeric Lactic Acids as Solubilizing Aids for HFA-Based Metered Dose Inhalers"; *1998 Conference of the American Association of Pharmaceutical Scientists,* San Francisco, California; Nov. 1998; 1 page.
Dunbar SA, Katz NP; "Chronic opioid therapy for nonmalignant pain in patients with a history of substance abuse: report of 20 cases." *Journal of Pain and Symptom Management.* 11(3); (1996) pp. 163-171.
Edimo, A., et al; "Capacity of Lipophilic Auxiliary Substances to Give Spheres by Extrusion-Spheronization"; *Drug Development and Industrial Pharmacy,* 19(7); (1993); pp. 827-842.
Eliasen, Helle, et al; "Effects of binder rheology on melt agglomeration in a high shear mixer"; *International Journal of Pharmaceutics 176;* (1998); pp. 73-83.
Fernandez, Sylvie, et al; "Lipolysis of the semi-solid self-emulsifying excipient Gelucire® 44/14 by digestive lipases"; *Biochimica et Biophysica Acta 1781;* (2008); pp. 367-375; available online Jun. 3, 2008.
Fitzgerald, B. P., et al., "Effect of Constant Administration of a Gonadotropin-Releasing Hormone Agonist on Reproductive Activity in Mares: Preliminary Evidence on Suppression of Ovulation During the Breeding Season"; *Am. J. Vet. Res.,* vol. 54, No. 10; Oct. 1993; pp. 1746-1751.

Fleury, J., et al., "Evaluation of the SABER Delivery System for the Controlled Release of Deslorelin for Advancing Ovulation in the Mare: Effects of Formulation & Dose", *Proceed Int'l. Symp. Control. Rel. Bioact. Mater.,* 25; (1998); Controlled Release Society, Inc.; pp. 657-658.
Gad, Shayne C., et al; "Nonclinical Vehicle Use in Studies by Multiple Routes in Multiple Species"; *International Journal of Toxicology,* 25; Sep. 20, 2006; pp. 1-23.
Gattefossé Corporation (1989); "To Help With Your Impossible Formulations: A Guide to Gattefossé Liquid Excipients"; 6 pages.
Gattefossé (1998); "Oral Route Excipients"; 8 pages.
GELUCIRE® 44/14 brochure (1999); "Immediate Release and Enhanced Bioavailability"; pp. 1-16.
GELUCIRE® Technical Dossier; "Answering the Need for Enhanced Bioavailability"; Oct. 1996; 16 pages.
GELUCIRE® (1996); "Answering the Need for Enhanced Bioavailability"; 5 pages.
"General Characteristics of Polymers"; Museum of Fine Arts, Boston; (2007); pp. 1-4.
Gibson, et al.; "Effects of Formulation Variables on Controlled Release of Paclitaxel and other Chemotherapeutic Agents from a Novel Delivery System" *AAPS New Orleans, LA;* (1999); Southern BioSystems, Inc. Birmingham AL, USA; 2 pages.
Gibson, et al.; "In Vitro and In Vivo Evaluation of a Novel In Situ-Forming Pareteral Delivery System"; *Meeting of Recent Advances in Drug Delivery Systems,* Salt Lake City UT; (1999); Southern BioSystems, Inc. Birmingham AL, USA; 2 pages.
Gilderman L., et al; "Remoxy™: A New Opioid Drug With Effective Analgesia and Abuse-Resistance." *American Pain Society Annual Meeting,* San Antonio, TX, May 2006; 1 page.
Ginther, O.J.; "Follicles"; *Ultrasonic Imaging and Reproductive Events in the Mare. EquiServices, Chapter 4;* Cross Plains, WI; (1986); pp. 43-72.
Ginther, O.J., "Effect of a Synthetic Gonadotropin-Releasing Hormone on Plasma Concentrations of Luteinizing Hormone in Ponies", *Am. J. Vet. Res.,* 1 vol. 35, No. x; Jan. 1974; pp. 79-8.
Ginther, O.J., "Reproductive Efficiency", *Reproductive Biology of the Mare Basic and Applied Aspects, Second Ed., Chapter 12;* (1992); pp. 499-509.
Glajchen, M.; "Chronic Pain: Treatment Barriers and Strategies for Clinical Practice."; *J AM Board Fam Pract.;* 14(3); (2001); pp. 212-218.
González et al; "Methylphenidate bioavailability from two extended-release formulations"; *International Journal of Clinical Pharmacology Therapeutics,* vol. 40, No. 4; (2002) pp. 175-184.
Gould, Phillip L.; "Salt selection for basic drugs"; *International Journal of Pharmaceutics,* 33 (1986); pp. 201-217.
Greydanus, D. E.; "Psychopharmacology for ADHD in Adolescents: Quo Vadis?"; *Psychiatric Times* vol. 20, No. 5; May 5, 2003; pp. 1-7.
Handbook of Pharmaceutical Excipients: Sixth Edition; "Medium-chain Triglycerides"; *Pharmaceutical Press and American Pharmacists Association 2009;* pp. 429-431.
Harrison, L.A., et al.; "Comaprison of HCG, Buserelin and Luprostiol for Induction of Ovulation in Cycling Mares"; *Equine Veterinary Science,* vol. 11, No. 3; (1991); pp. 163-166.
Hatakeyama et al.; "Synthesis and physical properties of polyurethanes from saccharide-based polycaprolactones"; *Macromolecular Symposia,* vol. 130; (1998); pp. 127-138.
Hauss, David J., et al; "Lipid-Based Delivery Systems for Improving the Bioavailability and Lymphatic Transport of a Poorly Water-Soluble $LTB_4$ Inhibitor"; *Journal of Pharmaceutical Sciences,* vol. 87, No. 2; Feb. 1998; pp. 164-169; published online Jan. 7, 1998.
Hays Lon R.; "A profile of OxyContin addiction"; *Journal of Addictive Diseases* 23(4); (2004); pp. 1-9.
He, Y., et al; "Oral Formulation of a Novel Antiviral Agent, PG301029, in a Mixture of Gelucire 44/14 and DMA (2:1, wt/wt)"; *AAPS Pharm. Sci. Tech.* 6(1); (2005); pp. E1-E5.
Henry, C.; "Sucrose Acetate Isobutyrate Special Grade for Beverage Applications" *International Food Ingred;* (1995); pp. 47-49.

(56) References Cited

OTHER PUBLICATIONS

Hoskin PJ, et al; "The bioavailability and pharmacokinetics of morphine after intravenous, oral and buccal administration in healthy volunteers."; *Br J Clin Pharmacol;* 27 (4); (1989); pp. 499-505.

Hülsmann, S., et al; "Melt extrusion—an alternative method for enhancing the dissolution rate of 17β-estradiol hemihydrate"; *European Journal of Pharmaceutics and Biopharmaceutics 49;* (2000); pp. 237-242.

Hyland, J.H., et al.; "Infusion of Gonadotrophin-releasing hormone (GnRH) Induces Ovulation and Fertile Oestrus in Mares During Seasonal Anoestrus"; *J. Reprod. Fert., Suppl. 35* (1987); pp. 211-220.

Inciardi James A, et al; "Mechanisms of prescription drug diversion among drug-involved club- and street-based populations"; *Pain Medicine.* 8(2), (2007); pp. 171-183.

Irvine, D.S., et al; "Duration of Oestrus and Time of Ovulation in Mares Treated with Synthetic GnRH (Ay24,031)"; *J. Reprod. Fert. Supp. 23;* (1975); pp. 279-283.

Irvine; "GnRH Clinical Application"; *In Equine Reproduction,* (eds) McKinon, A.O. and Voss. J.L., Chapter 36, Lea & Febiger; (1993); pp. 41-45.

Ishida T, Oguri K, et al; "Isolation and identification of urinary metabolites of oxycodone in rabbits"; *Drug Metab Dispos;* 7(3); (1979); pp. 162-165.

Ishida T, Oguri K, Yoshimura H.; "Determination of oxycodone metabolites in urines and feces of several mammalian species"; *J Pharmacobiodyn;* 5(7); (1982); pp. 521-525.

Itoh, K., et al; "Improvement of physiochemical properties of N-4472 part I formulation design by using self-microemulsifying system"; *Int .J. Pharm.,* 238); (2002); pp. 153-160.

Iwanaga, Kazunori, et al; "Disposition of Lipid-Based Formulation in the Intestinal Tract Affects the Absorption of Poorly Water-Soluble Drugs"; *Biol. Pharm. Bull.* vol. 29, No. 3; (2006); pp. 508-512, published online Dec. 5, 2005.

Iyakuhin Tenkabutsu Kenkyykai Ed.; "Jitsuyo Iyakuhin Tenkabutsu (Practical Medical Additives)"; pub. *Kagaku Kogyo-sha;* Mar. 5, 1974; Tokyo; 6 pages.

Jannin, V., et al; "Systemes auto-émulsionnables et émulsions séches"; *STP Pharma Pratiques,* vol. 15, No. 3; May/Jun. 2005; pp. 246-255.

Jannin, V., et al; "Approaches for the development of solid and semi-solid lipid-based formulations"; *Advanced Drug Delivery Reviews 60;* (2008); pp. 734-746; available online Nov. 4, 2007.

Japanese Office Action for Japanese Application No. 2010-537128, dated Jun. 5, 2013.

Jöchle, W., et al.; "Control of Ovulation in the Mare with Ovuplant a Short-Term Release Implant (STI) Containing the GnRH Analogue Deslorelin Acetate: Studies from 1990 to 1994"; *Journal of Equine Veterinary Science,* vol. 14m No. 12; (1994); pp. 632-644.

Johnson, et al; "Biodegradable Delivery Systems for Estradiol: Comparison Between Poly(DL-Lactide) Microspheres and the Saber Delivery System"; *Proceed. Int'l Symp. Control. Rel. Bioact. Mater.,* 26; Controlled Release Society, Inc.; (1999); 1 page.

Johnson, R.M., et al; "Applications of Continuous Site-Directed Drug Delivery"; *Proc. West Pharmacol Soc.* vol. 45; (2002); pp. 219-222.

Johnston Lloyd D, et al; "Monitoring the future. National results on adolescent drug use: overview of key findings"; *(NIH Publication No. 05-5726).* Bethesda, MD: National Institute on Drug Abuse; (2004); pp. 1-66.

Kaiko; "Pharmacology of Tablets of Oxycontin the Development Process Thereof"; *Palliative Care Research* 7(1); (2005); pp. 3-13.

Kale, A., et al; "Design and Evaluation of Self-Emulsifying Drug Delivery Systems (SEDDS) of Nimodipine"; *AAPS Pharm. Sci. Tech.,* 9(1); (2008); pp. 191-196.

Kamel S., et al; "Pharmaceutical significance of cellulose: A review"; *eXPRESS Polymer Letters* vol. 2, No. 11; (2008); pp. 758-778.

Kane, Anil, et al; "A Statistical Mixture Design Approach for Formulating Poorly Soluble Compounds in Liquid Filled Hard Shell Capsules"; *Bulletin Technique Gattefosse* No. 99; (2006); pp. 43-49.

Karatas, A., et al; "Improved solubility and dissolution rate of piroxicam using gelucire 44/14 and labrasol"; *II Farmaco 60(9);* (2005); pp. 777-782; available online Aug. 9, 2005.

Katz NP, et al.; "Behavioral monitoring and urine toxicology testing in patients receiving long-term opioid therapy" *Anesth Analg.* 97(4); (2003); pp. 1097-1102.

Katz NP, et al; "Development and preliminary experience with an ease of extractability rating system for prescription opioids"; *Drug Development and Industrial Pharmacy.* 32(6); (2006); pp. 727-746.

Katz NP, et al; "Prescription monitoring of medical and non-medical Schedule II opioid abuse in Massachusetts: 1996-2005"; *Conference paper presented at the 69th College on Problems of Drug Dependence (CPDD),* Quebec, Canada; (2007); 1 page.

Katz NP, et al; "Challenges in the development of prescription opioid abuse-deterrent formulations"; *Clin J Pain,;* 23(8); (2007); pp. 648-660.

King; "Tablets, Capsules, and Pills" Remington's Pharmaceutical Sciences, Ed. Arthur Osol, Chapter 89, (1980); pp. 1553-1584.

Koga, Kenjiro, et al; "In vitro and in situ evidence for the contribution of Labrasol® and Gelucire 44/14 on transport of cephalexin and cefoperazone by rat intestine"; *European Journal of Pharmaceutics and Biopharmaceutics 54;* (2002); pp. 311-318.

Kulkarni, et al., "Polyactic Acid for Surgical Implants," *Arch. Surg.* vol. 93; (1966); pp. 839-843.

Lacoste, D., et al.; "Reversible Inhibition of Testicular Androgen Secretion by 3-, 5- and 6-Month Controlled-Release Microsphere Formulations of the LH-RH Agonist [D-Trp.sup.6, des-Gly-NH.sub.2]LH-RH Ethylamide in the Dog"; *J. Seroid Biochem.* vol. 33, No. 5; (1989); pp. 1007-1011.

Laforet, Jean-Pierre, et al; "The Right Mix"; *Gattefosse,* vol. 7, No. 1; (1995); pp. 1-10.

Lalovic Bojan, et al; "Pharmacokinetics and pharmacodynamics of oral oxycodone in healthy human subjects: role of circulating active metabolites"; *Clin Pharmacol Ther* 79 (5); (2006); pp. 461-479.

Larsen, A., et al; "In vitro evaluation of Pharmaceutical surfactants fate during lipolysis and its effects on solubilization of a poorly soluble model compound: Danazol"; *Conference on When Poor Solubility Becomes an Issue: From Early Stage to Proof of Principles;* (2006); Verona (Italy); 2 pages.

Larsen, Anne, et al; "Pharmaceutical Surfactants in Biorelevant Media: Impact on Lipolysis and Solubility of a Poorly Soluble Compound; Danazol"; *Conference, $5^{th}$ World Meeting on Pharmaceutics Biopharmaceutics and Pharmaceutical Technology,* Geneva, Switzerland; (2006); 2 pages.

Lopez et a;. "Comparative efficacy of two once daily methylphenidate formulations (Ritalin LA and Concerta) and placebo in children with attention deficit hyperactivity disorder across the school day"; *Pediatr Drugs* 5 (8); (2003); pp. 545-555.

Lowden, K.; "Filling hard gelatin capsules: experience in a new environment"; *Pharmaceutical Manufacturing Review,* vol. 10, No. 5; (1998); pp. 27-29.

Loy, R.G., et al; "The Effects of Human Chorionic Gonadotrophin on Ovulation, Length of Estrus, and Fertility in the Mare"; University of California, Davis, California, Jan. 30, 1965; pp. 41-50.

Malhotra Bimal K. et al; . "The pharmacokinetics of oxycodone and its metabolites following single oral doses of Remoxy®, an abuse-deterrent formulation of extended-release oxycodone, in patients with hepatic or renal impairment"; *Journal of Opioid Management* 11:2; Mar./Apr. 2015; pp. 157-169.

Markowitz et al; "Advances in the pharmacotherapy of attention-deficit-hyperactivity disorder: focus on methylphenidate formulations"; *Pharmacotherapy* 23 (10); (2003); pp. 1281-1299.

Markowitz et al; "Pharmacokinetics of methylphenidate after oral administration of two modified-release formulations in healthy adults"; *Clin Pharmacokinet* 42(4); (2003); pp. 393-401.

Material Safety Data Sheet "Eastman: Cellulose Acetate Butyrate CAB-381-2 BP CAB381-20 BP: Coating Chemicals" Eastman Chemical Company, Publication E-296B, Aug. 1994.

(56) References Cited

OTHER PUBLICATIONS

Material Safety Data Sheet "Eastman: Cellulose Esters for Pharmaceutical Drug Delivery" Eastman Chemical Company, Publication PCI-105B, Jun. 2004.
Material Safety Data Sheet of Eastman Chemical Products, "SAIB" Sucrose Acetate Isobutyrate, pp. 1-24. Publication GN-311F (Jun. 2004).
Material Safety Data Sheet of Eastman Fine Chemical Pharmaceutical Ingredients, Sucrose Acetate Isobutyrate Special Grade (SAIB-SG), Publication No. EFC-211, (May 1991).
Material Safety Data Sheet of Eastman Products for the Food Industry, "Sucrose Acetate Isbutyrate (SAIB-SB) for Use in Fruit-Flavored Beverages," Publication No. ZM-90, (Sep. 1989); pp. 2-7.
McCabe SE, et al; "Motives, diversion and routes of administration associated with nonmedical use of prescription opioids"; *Addictive Behaviors.* 32; (2007); pp. 562-575.
McCarthy, P.F., et al.; "Management of Stallions on Large Breeding Farms"; *Veterinary Clinics of North America: Equine Practice,* vol. 8, No. 1; Apr. 1992; pp. 219-235.
McKinnon, A.O., et al.; "Effect of GnRH Analogue (Ovuplant), hCG and Dexamethasone on Time to Ovulation in Cycling Mares"; World Equine Veterinary Review, vol. 2: No. 3; (1997); pp. 16-18.
McKinnon, A.O., et al.; "Repeated Use of a GnRH Analogue Deslorelin (Ovuplant) for Hastening Ovulation in the Transitional Mare"; *Equine Veterinary Journal* 29 (2); (1996); pp. 153-155.
McLellan AT, et al; An improved diagnostic instrument for substance abuse patients—The Addiction Severity Index: *The Journal of Nervous and Mental Disease.* vol. 168, No. 1; (1980); pp. 26-33.
Mearns, D.; "Changing Seasons"; *The Blood-Horse;* Sep. 28, 1996; pp. 4794-4765.
Meehan, E., et al; "Monitoring the stability of excipients used in lipid matrix formulations"; *(Poster Abstract), Conference "33rd Annual Meeting of the Controlled Release Society",* Vienna, Austria. Jul. 22, 2006; 2 pages.
Mehuys, E., et al; "Human bioavailability of propranolol from a matrix-in-cylinder system with a HPMC-Gelucire® core"; *Journal of Controlled Release 107;* (2005); pp. 523-536; available online Aug. 1, 2005.
Merrifield, Bruce; "Solid Phase Synthesis"; *Science,* vol. 232; Apr. 18, 1986; pp. 341-347.
Meyer RJ, Hussain AS. Awareness topic: mitigating the risk of ethanol induced dose dumping from oral sustained/controlled release dosage forms. In: FDA's Advisory Committee for Pharmaceutical Science Meeting, Oct. 2005; pp. 1-4.
Montovan, S.M. et al; "The Effect of a Potent GnRH Agonist on Gonadal and Sexual Activity in the Horse"; *Theriogenology,* vol. 33 No. 6; Jun. 1990; pp. 1305-1321.
Mumford, E.L.; "Use of Deslorelin Short-Term Implants to Induce Ovulation in Cycling Mares During Three Consecutive Estrous Cycles"; *Animal Reproduction Science,* vol. 39; (1995); pp. 129-140.
Murray Sally, et al; "Alcohol-associated rapid release of a long-acting opioid"; *CMAJ;* 173(7); Sep. 27, 2005; pp. 756.
Nabors, et al; "Controlled Release of Diclofenac-Na from Cellulose Ester Microspheres"; *PDD Presentation 7481 at the 1994 Ninth Annual AAPS Meeting in San Diego, CA;* Nov. 6-10, 1994; 2 pages.
Nakagaki, Arita; "Seizai Butsuri Kagaku (Physical Chemistry of Medical Preparations)", pub. *Asakura Shoten;* Nov. 5, 1968; Tokyo; 6 pages.
Nally, J., et al.; "Induction of Mucosal IgA Specific for SeMF3 for *Streptococcus equi* with Intranasal Vaccination Using a Sucrose Acetate Isobutyrate Based Delivery System", *Proceed. Int'l. Symp. Control. Rel. Bioact. Mater.,* 26; (1999); Controlled Release Society, Inc. 2 pages.
"NATROSOL® Hydroxyethylcellulose A Nonionic Water-Soluble Polymer"; *Hercules Incorporated, Aqualon Division;* (1999); pp. 1-24.
Nett, T.M., et al.; "Further Studies on the Radioimmunoassay of Gonadotropin-releasing Hormone: Effect of Radioiodination, Antiserum and Unextracted Serum on Levels of Immunoreactivity in Serum"; *Endocrinology* vol. 101, No. 4, (1977); pp. 1135-1144.
O'Driscoll, Caitriona M.; "Lipid-based formulations for intestinal lymphatic delivery"; *European Journal of Pharmaceutical Sciences 15;* (2002); pp. 405-415.
Okumu, et al; "Evaluation of SABER™ as a Local Delivery System for rhVEGF-Formulation Design and In Vitro Assessment" *Genentech, Inc., South San Francisco, CA USA and Southern BioSystems, Inc. Birmingham AL, USA;* (2000); 1 page.
Okumu, et al; "Evaluation of SABER™ as a Local Delivery System for rhVEGF-Formulation Design and In Vitro Assessment" *Genentech, Inc., South San Francisco, CA USA and Southern BioSystems, Inc. Birmingham AL, USA.* Poster; (2001); 1 page.
Patel, Pranav, et al; "Preparation, Evaluation and Comparison of Lipid Based Drug Delivery Systems of Tacrolimus"; *International Journal of Pharmacy and Pharmaceutical Sciences,* vol. 6 Suppl 2; (2014); pp. 588-591.
Patrick et al; "New methylphenidate formulations for the treatment of attention-deficit/hyperactivity disorder" *Expert Opin Drug Deliv* 2(1); (2005); pp. 121-143.
Pelham et al; "Once-a-day Concerta methylphenidate versus three-times-daily methylphenidate in laboratory and natural settings"; *Pediatrics* vol. 107, No. 6; Jun. 6, 2001; pp. 1-15.
Perissutti, B.; et al; "Solid dispersions of carbamazepine with Gelucire 44/14 and 50/13"; *S.T.P. Pharma Sciences* 10(6); (2000); pp. 479-484.
Pozzi, Franco, et al; "Formulations of Ubidecarenone with Improved Bioavailability"; *Eur. J. Pharm. Biopharm,* vol. 37, No. 4; (1991); pp. 243-246.
Pulido et al.; "Enzymatic Regioselective Acylation of Hexoses and Pentoses Using Oxime Esters"; *J. Chem. Soc. Perkin Trans.* 1, (21); (1992); pp. 2891-2898.
Rabb et al.; "Effects of Active Immunication Against GnRH on LH, FSH and Prolactin Storage, Sectretion and Response to Their Secretagogues in Pony Geldings"; *J. Anim. Sci.,* 68; (1990); pp. 3322-3329.
Ren, Shan, et al; "In Vitro Metabolic Stability of Moisture-Sensitive Rabeprazole in Human Liver Microsomes and Its Modulation by Pharmaceutical Excipients"; *Arch Pharm Res* vol. 31, No. 3; (2008); pp. 406-413; published online Apr. 13, 2008.
Reynolds, R.C. et al.; "Sucrose acetate isobutyrate (SAIB): historical aspects of its use in beverages and a review of toxicity studies prior to 1988"; *Food Chem. Toxicol.*36(2), (1998); pp. 81-93.
Reynolds, R.C.; "Metabolism and pharmacokinetics of sucrose acetate isobutyrate (SAIB) and sucrose octaisobutyrate (SOIB) in rats, dogs, monkeys or humans: a review"; *Food Chem. Toxicol.,* 36 (2); (1998); pp. 95-99.
Robinson; "Coating of Pharmaceutical Dosage Forms" *Remington's Pharmaceutical Sciences,* Ed. Arthur Osol, Chapter 90; (1980); pp. 1585-1593.
Roser, J.J., et al.; "The Development of Antibodies to Human Chorionic Gonadotrpins Following its Repeated Injection in the Cyclic Mare"; J. Reprod. Fert Suppl., (1979); pp. 173-179.
Roussin, P. et al; Gelucire® 44/14; "A High-Performance System to Enhance Bioavailability of Poorly Water Soluble Drugs"; *Bulletin Technique Gattefosse,* No. 90; (1997); pp. 51-58.
Sachs-Barrable, K., et al; "Lipid Excipients Peceol and Gelucire 44/14 decrease P-glycoprotein mediated efflux of Rhodamine 123 partially due to modifying P-glycoprotein expression within Caco-2 Cells."; *J. Pharm. Pharm. Sci.,* 10(3); (2007); pp. 319-331.
Saeio, Kiattisak, et al; "Factors Influencing Drug Dissolution Characteristic From Hydrophilic Polymer Matrix Tablet"; *Scientia Pharmaceutica (Sci. Pharm.)* 75; (2007); pp. 147-163.
Saeki; "Progress of Orally Opiate Analgesics and Non-Steroidal Anti-Flammatory Agent" *Drug Deliv Syst* 20(5); (2005) pp. 521-529.
Santus et al.; "Osmotic Drug Delivery: A Review of the Patent Liter" *J Control Release* 35(1); (1995); pp. 1-21.
Schamp, Karen, et al; "Development of an in vitro/in vivo correlation for lipid formulations of EMD 50733, a poorly soluble, lipophilic drug substance"; *European Journal of Pharmaceutics and Biopharmaceutics 62;* (2006); pp. 227-234; available online Oct. 24, 2005.

(56) References Cited

OTHER PUBLICATIONS

Selimovic, Seila, and Hu Yue; "Aging Effects in Suspensions of Silica Particles"; *Mat. Res. Soc. Symp. Proc., vol. 790 Materials Research Society;* (2004) pp. P7.11.1-P7.11.6.

Serajuddin, Abu T.M., et al; "Effect of Vehicle Amphiphilicity on the Dissolution and Bioavailability of a Poorly Water-Soluble Drug from Solid Dispersions"; *Journal of Pharmaceutical Sciences,* vol. 77, No. 5, May 1988; pp. 414-417.

Serajuddin, Abu T.M., et al; "Water SETNIKMigration from Soft Gelatin Capsule Shell to Fill Material and Its Effect on Drug Solubility"; *Journal of Pharmaceutical Sciences,* vol. 75, No. 1; Jan. 1986; pp. 62-64.

Sethia, Sundeep, et al; "Physicochemical Characterization of Solid Dispersions of Carbamazepine Formulated by Supercritical Carbon Dioxide and Conventional Solvent Evaporation Method"; *Journal of Pharmaceutical Sciences,* vol. 91, No. 9; Sep. 2002; pp. 1948-1957.

Sethia, Sundeep, et al; "In Vitro-In Vivo Evaluation of Supercritical Processed Solid Dispersions: Permeability and Viability Assessment in Caco-2 Cells"; *Journal of Pharmaceutical Sciences,* vol. 93, No. 12; Dec. 2004; pp. 2985-2993; published online Oct. 1, 2004.

Shah, N. H; et al; "Self-Emulsifying Drug Delivery Systems (SEDDS) for Improving In Vitro Dissolution and Oral Absorption of Lipophilic Drugs"; *Bulletin Technique. Gattefossé Report,* No. 85; (1992/93); pp. 45-54.

Sheen, Pai-Chang, et al; "Bioavailability of a Poorly Water-Soluble Drug from Tablet and Solid Dispersion in Humans"; *Journal of Pharmaceutical Sciences,* vol. 80, No. 7; Jul. 1991; pp. 712-714.

Shimpi, Shyam, et al; "Preparation and Evaluation of Diltiazem Hydrochloride-Gelucire 43/01 Floating Granules Prepared by Melt Granulation"; *AAPS PharmSciTech* 5(3), Article 43, (http://www.aapspharmscitech.org); (2004); pp. 1-6; published online Jul. 12, 2004.

Smith, Dawn A., et al; "A Novel Parental Delivery System" *AAPS Presentation PDD 7270,* Seattle, WA; (1996) Annual Meeting; 2 pages.

Soliman, M. S., et al; "Preparation and in vitro characterization of a semi-solid dispersion of flurbiprofen with Gelucire 44/14 and Labrasol"; *Pharmazie* 60(4); (2005); pp. 288-293.

Srinivas et al.; "Enantioselective pharmacokinetics and pharmacodynamics of dl-threo-methylphenidate in children with attention deficit hyperactivity disorder"; *Clin Pharmacal Ther* 52(5); (1992); pp. 561-568.

Stegemann. S., et al; "When Poor Solubility Becomes an Issue: From Early Stage to Proof of Concept"; *European Journal of Pharmaceutical Sciences 31;* (2007); pp. 249-261.

Strickley, Robert G; "An Overview of Lipid Excipients Currently Available: Strengths, Weaknesses and Opportunity Gaps: The Options for the Formulator"; *Bulletin Technique Gattefosse,* No. 100; (2007); pp. 31-37.

Strickley, Robert G.; "Solubilizing Excipients in Oral and Injectable Formulations"; *Pharmaceutical Research,* vol. 21, No. 2; Feb. 2004; pp. 201-230.

Subramanian, Ramaswamy, et al; "Effect of Lipid Excipients on In Vitro Pancreatic Lipase Activity"; *Drug Development and Industrial Pharmacy,* vol. 29, No. 8; (2003); pp. 885-890.

Sucrose Acetate Isobutyrate, 21 CFR 172.831 (1999).

Sullivan, et al; "Delivery of Taxol® and other Antineoplastic Agents from a Novel System Based on Sucrose Acetate Isobutyrate" *AAPS Boston, MA. Southern BioSystems, Inc.* Birmingham AL, USA (1997); 2 pages.

Sullivan, et al; "Sustained Release of Orally Administered Active Using SABER Delivery System Incorporated into Soft Gelatin Capsules"; *Proceed Int'l. Control. Rei. Bioact. Mater. Controlled Release Society.* vol. 25; Jun. 1998 Las Vegas NV; pp. 918-919.

Sullivan, et al; "Sustained Release of Progesterone and Estradiol from the SABER™ Delivery System: In Vitro and In Vivo Release Rates" *CRS Las Vegas, NV. Southern BioSystems, Inc.* Birmingham AL, USA; (1998); 2 pages.

Sullivan, et al; "Sustained Release of Lysozyme from the SABER™ Delivery System" *AAPS, New Orleans, LA. Southern BioSystems, Inc.* Birmingham AL, USA; (1999); 2 pages.

Sullivan, et al; "Incorporation of Polymer Microparticles Into Sucrose Acetate Isobutyrate Reduces Burst and Extends Release" *Proceed. Int'l Symp. Control. Rel. Bioact. Mater., 27, Controlled Release Society, Inc.* Paris, France; Jul. 7-13, 2000.

Sullivan, J. J., et al.; "Duration of Estrus and Ovulation Time in Nonlactating Mares Given Human Chorionic Gonadotropin During Three Successive Estrous Periods"; *J.A.V.M.A.,* vol. 162, No. x; May 15, 1973; pp. 895-898.

Svensson, A., et al; "Hydration of an amphiphilic excipient Gelucire® 44/14"; *Int. J. Pharm.* 281 (1-2); (2004); pp. 107-118.

Swanson et al; "Objective and subjective measures of the pharmacodynamic effects of Adderall in the treatment of children with ADHD in a controlled laboratory classroom setting"; *Psychopharmacol Bull* 34(1); (1998); pp. 55-60.

Swanson et al; "Acute tolerance to methylphenidate in the treatment of attention deficit hyperactivity disorder in children" *Clin Pharmacal Ther* 66(3); (1999); pp. 295-305.

Swanson et al. Ritalin: Theory and Practice. 2nd Edition, Greenhill & Osman Ed., Mary Ann Lieber, Larchmont, NY; (1999) pp. 405-430.

Swanson et al; "Efficacy of a new pattern of delivery of methylphenidate for the treatment of ADHD: effects on activity level in the classroom and on the playground" *J Am Acad Child Adolesc Psychiatry* 41(11); (2002); pp. 1306-1314.

Swanson et al; "Pharmacokinetic and pharmacodynamic properties of stimulants: implications for the design of new treatments for ADHD"; *Behav Brain Res* 130(1-2); (2002); pp. 73-78.

Swanson et al; "Development of a new once-a-day formulation of methylphenidate for the treatment of attention-deficit/hyperactivity disorder: proof-of-concept and proof-of-product studies"; *Arch Gen Psychiatry* 60(2); (2003); pp. 204-211.

Swanson et al; "Serum and brain concentrations of methylphenidate: implications for use and abuse"; *Neurosci Biobehav Rev* 27(7); (2003); pp. 615-621.

Swanson et al; "A comparison of once-daily extended-release methylphenidate formulations in children with attention-deficit/hyperactivity disorder in the laboratory school (the Comacs Study)"; *Pediatrics* 113 (3 Pt. 1); (2004); pp. e206-e216.

Swiderski et al.; "Application of 14C Isotope in Studies on the Lability of Sugar Substituents" *Nukleonika, Supl.,* vol. 10; (1966); pp. 347-352.

Tashtoush; Bassam M., et al; "In Vitro and In Vivo Evaluation of Glibenclamide in Solid Dispersion Systems"; *Drug Development and Industrial Pharmacy,* vol. 30, No. 6; (2004); pp. 601-607.

Thompson, D. L., et al., "Effects of Melatonin and Thyrotropin Releasing Hormone on Mares During the Nonbreeding Season", Journal of Animal Science, vol. 56, No. 3, (1983), pp. 668-677.

Thompson, D. L., et al., "Testosterone Effects on Mares During Synchronization with Altrenogest: FHS, LH, Estrous Duration and Pregnancy Rate"; *Journal of Animal Science,* vol. 56, No. 3; (1983); pp. 678-686.

Tipton; "Peptide Delivery from an In Situ Gelling System Based lon Sucrose Acetate Isobutyrate" *AAPS J Abstract. Southern BioSystems, Inc.* Birmingham AL, USA; (1999); 1 page.

Tipton, "In Situ Gelling Systems"; Sustained-Release Injectable Products, Ed. Senior & Radomsky, Interpharm Press, Denver, CO; (2000); pp. 258-259.

Tipton, et al; "Local Delivery from a Novel Biodegradable in Situ Delivery System"; *Sixth World Biomaterials Congress, Kamuela, HI,. Southern BioSystems, Inc.* Birmingham AL, USA, May 15-20, 2000; 1 page.

Tran, Thao Truong-Dinh; et al; "Dissolution-modulating mechanism of alkalizers and polymers in a nanoemulsifying solid dispersion containing ionizable and poorly water-soluble drug"; *European Journal of Pharmaceutics and Biopharmaceutics 72;* (2009); pp. 83-90; available online Dec. 25, 2008.

Trescot AM, et al; "Opioid Guidelines in the Management of Chronic Non-Cancer Pain." *Pain Physician,* vol. 9; (2006), pp. 1-40.

(56) References Cited

OTHER PUBLICATIONS

U.S. Department of Health and Human Services "Guidance for Industry: Food-Effect Bioavailability and Fed Bioequivalence Studies" FDA, Center for Drug Evaluation and Research (CDER), Dec. 2002.
U.S. Appl. No. 12/754,486, filed Apr. 5, 2010, 103 pages; with Preliminary Amendment filed Nov. 23, 2010, 13 pages.
U.S. Appl. No. 60/434,839, filed Dec. 18, 2002, 111 pages.
Vega-Rios Aracelly, et al; "Acid-catalyzed hydrolysis of triacylglycerols obeys monoexponential kinetics."; *International Journal of Chemical Kinetics,* vol. 24; (1992); pp. 887-894.
Venkatesan, N. et al; "Gelucire® 44/14 and Labrasol® in Enhancing Oral Absorption of Poorly Absorbable Drugs"; *Bulletin Technique Gattefosse,* No. 99; (2006); pp. 79-88.
Vila Jato, J.L., et al; "Influence of melting point and HLB on the release of amoxicillin from granulates containing Gelucire as excipients"; *S.T.P. Pharma,* vol. 6, No. 5; (1990); pp. 287-292.
Volkow et al; "Relationship between psychostimulant-induced 'high' and dopamine transporter occupancy"; *Proc Natl Acad Sci USA* 93(19); (1996); pp. 10388-10392.
Volkow et al. "Temporal relationships between the pharmacokinetics of methylphenidate in the human brain and its behavioral and cardiovascular effects"; *Psychopharmacology 123;* (1996) pp. 26-33.
Volkow et al; "Methylphenidate and cocaine have a similar in vivo potency to block dopamine transporters in the human brain"; *Life Sciences* vol. 65, No. 1; (1999); PL7-PL12.
Volkow et al; "Relationship between blockade of dopamine transporters by oral methylphenidate and the increases in extracellular dopamine: therapeutic implications"; *Synapse* 43(3); (2002); pp. 181-187.
Volkow, et al; "Dopamine transporter occupancies in the human brain induced by therapeutic doses of oral methylphenidate"; *Am J Psychiatry* 155(10); (1998); pp. 1325-1331.
Voss, J.L., et al; "The Effect of HCG on Duration of Oestrus, Ovulation Time and Fertility in Mares"; *Journal of Reprod. Fert.,* Suppl. 23; (1975); pp. 297-301.
Wigal et al; "Reliability and validity of the SKAMP rating scale in a laboratory school setting" *Psychopharmacol Bulletin,* vol. 34, No. 1; (1998); pp. 47-53.
Wigal et al; "Selection of the Optimal Dose Ratio for a Controlled-Delivery Formulation of Methylphenidate"; *The Journal of Applied Research 3;* (2003); pp. 46-63.
Wightman et al; "Transient changes in mesolimbic dopamine and their association with 'reward'"; *Journal of Neurochemistry* 82(4); (2002); pp. 721-735.
Wolraich et al; "Randomized, controlled trial of oros methylphenidate once a day in children with attention-deficit/hyperactivity disorder"; *Pediatrics* 108(4); (2001); pp. 883-892.
Yüksel, Nilüfer, et al; "Enhanced bioavailability of piroxicam using Gelucire 44/14 and Labrasol: in vitro and in vivo evaluation"; *European Journal of Pharmaceutics and Biopharmaceutics 56;* (2003); pp. 453-459.
Friedmann N, Klutzaritz V, Webster L. Efficacy and safety of an extended-release oxycodone (Remoxy) formulation in patients with moderate to severe osteoarthritic pain. J Opioid Manag. 2011; 7(3):193-202.
Friedmann N, Klutzaritz V, Webster L. Long-term safety of Remoxy(R) (extended-release oxycodone) in patients with moderate to severe chronic osteoarthritis or low back pain. Pain Med. 2011; 12(5):755-760.
Setnik B, Roland CL, Cleveland JM, Webster L. The abuse potential of Remoxy((R)), an extended-release formulation of oxycodone, compared with immediate- and extended-release oxycodone. Pain Med. 2011; 12(4):618-631.
Zamloot M, Chao W, Kang L, Ross L, Fu R. Remoxy®: a novel formulation of extended-release oxycodone developed using the ORADUR® technology. J Appl Res. 2010; 10(3):88-96.
Webster LR. PTI-821: sustained-release oxycodone using gel-cap technology. Expert Opin Investig Drugs. 2007; 16(3):359-366.

\* cited by examiner

X03514: SAIB/EL/IM/CAB 381-20 (65/27/3.5/4.5)

X03515: SAIB/EL/IM/CAB 381-20 (65/27/3/5)

X03516: SAIB/EL/IM/CAB 381-20 (63/29/3/5)

X03517: SAIB/EL/IM/CAB 381-20 (63/29/3.5/4.5)

(all contained 12 mg/ml Oxycodone base)

X03511 = 59.3; 31.4; 1; 8.6 SAIB; EL; IM; CAB-381-20BP 9mg/g OC

X03512 = 59.8; 31.4; 1; 7.8 SAIB; EL; IM; CAB-381-20BP 9mg/g OC

X03713 = 71; 23; 1; 5 SAIB; EL; IM; CAB-381-20BP 9mg/g OC

Dog Plasma pK Study

ORAL DRUG DELIVERY SYSTEM

This application claims the benefit of U.S. Provisional Application No. 60/433,116, filed Dec. 13, 2002, and of U.S. Provisional Application No. 60/517,464, filed Nov. 4, 2003.

FIELD OF THE INVENTION

The invention relates to dosage forms comprising formulations of drugs. More specifically, this invention relates to formulations that include High Viscosity Liquid Carrier Materials (HVLCMs) and their use to deliver drugs.

BACKGROUND

Techniques and compositions for drug delivery of pharmaceuticals, including oral delivery, are well known. For example antihistamines, decongestants and antacids are all commonly delivered in solid tablet form. Analgesics have been delivered orally in tablet form for many years, for example salicylic acid, morphine, Demerol™ (meperidine), codeine and Percocet™ (oxycodone). Controlled release and sustained release pharmaceutical compositions have also been available for many years; for example the Contac 400 Time Capsule™ (Phenylpropanolamine Hydrochloride and Chlorpheniramine Maleate), anti-psychotics, melatonin formulations provide release of an active agent over several hours. Analgesics are of particular interest for controlled release formulations, and common controlled release formulations for analgesics include the OxyContin® (oxycodone), MS Contin™ (morphine), CS Contin™ (codeine).

Formulation of drugs for delivery, particularly oral delivery, poses certain challenges. One challenge is to produce an oral controlled-release dosage form that provides for a relatively steady dose of drug over the approximately eight hours during which the dosage form passes through the gastrointestinal tract. Sustained release is often achieved by providing the tablet with a coating that delays release, or by formulating the tablet in such a way that it disintegrates relatively slowly, releasing drug as it does so. A tablet, however, once ingested, is subject to considerable mechanical and chemical stresses as it passes through the esophagus, stomach, duodenum, jejunum, ileum, large intestine and colon, thus providing a significant challenge in maintaining controlled release of the drug formulation. Acids, enzymes and peristalsis can cause the tablet to break apart, resulting in exposure of the inside of the tablet and an increase in surface area of the tablet material. This will tend to increase the delivery rate of the drug or otherwise adversely affect the controlled release properties of the dosage form.

Another challenge, is to produce a dosage form, including an oral dosage form, that reduces the potential for drug abuse. In particular, opioids, CNS-depressants, and stimulants are commonly abused. According to a 1999 study by the National Institute on Drug Abuse (NIDA), an estimated 4 million people, about 2 percent of the population age 12 and older, were (at the time of the study) using prescription drugs "non-medically." Of these, 2.6 million misused pain relievers, 1.3 million misused sedatives and tranquilizers, and 0.9 million misused stimulants.

While many prescription drugs can be abused, the most common classes of abused drugs are: (1) Opioids—often prescribed to treat pain, (2) CNS Depressants—used to treat anxiety and sleep disorders, and (3) Stimulants—prescribed to treat narcolepsy and attention deficit/hyperactivity disorder.

Opioids are a class of potent narcotics that includes, for example, morphine, codeine, oxycodone and fentanyl and related drugs. Morphine is often used to alleviate severe pain. Codeine is used for milder pain. Other examples of opioids that can be prescribed to alleviate pain include oxycodone (e.g. OxyContin®—an oral, controlled release form of the drug); propoxyphene (e.g. Darvon™); hydrocodone (e.g. Vicodin™); hydromorphone (e.g. Dilaudid™); and meperidine (e.g. Demerol™).

In addition to relieving pain, opioids can also produce a sensation of euphoria, and when taken in large doses, can cause severe respiratory depression which can be fatal.

CNS depressants slow down normal brain function by increasing GABA activity, thereby producing a drowsy or calming effect. In higher doses, some CNS depressants can become general anesthetics, and in very high doses may cause respiratory failure and death. CNS depressants are frequently abused, and often the abuse of CNS depressants occurs in conjunction with the abuse of another substance or drug, such as alcohol or cocaine. Many deaths occur yearly through such drug abuse. CNS depressants can be divided into two groups, based on their chemistry and pharmacology: (1) Barbiturates, such as mephobarbital (e.g. Mebaral™) and pentobarbital sodium (e.g. Nembutal™), which are used to treat anxiety, tension, and sleep disorders. (2) Benzodiazepines, such as diazepam (e.g. Valium™), chlordiazepoxide HCl (e.g. Librium™), and alprazolam (e.g. Xanax™), which can be prescribed to treat anxiety, acute stress reactions, and panic attacks. Benzodiazepines that have a more sedating effect, such as triazolam (e.g. Halcion™) and estazolam (e.g. ProSom™) can be prescribed for short-term treatment of sleep disorders.

Stimulants are a class of drugs that enhance brain activity—they cause an increase in alertness, attention, and energy that is accompanied by increases in blood pressure, heart rate, and respiration. Stimulants are frequently prescribed for treating narcolepsy, attention-deficit hyperactivity disorder (ADHD), and depression. Stimulants may also be used for short-term treatment of obesity, and for patients with asthma.

Stimulants such as dextroamphetamine (Dexedrine™) and methylphenidate (Ritalin™) have chemical structures that are similar to key brain neurotransmitters called monoamines, which include norepinephrine and dopamine. Stimulants increase the levels of these chemicals in the brain and body. This, in turn, increases blood pressure and heart rate, constricts blood vessels, increases blood glucose, and opens up the pathways of the respiratory system. In addition, the increase in dopamine is associated with a sense of euphoria that can accompany the use of these drugs.

Taking high doses of a stimulant can result in an irregular heartbeat, dangerously high body temperatures, and/or the potential for cardiovascular failure or lethal seizures.

Taking high doses of some stimulants repeatedly over a short period of time can lead to hostility or feelings of paranoia in some individuals.

A common and particularly dangerous cocktail of drugs is produced when stimulants are mixed with antidepressants or over-the-counter cold medicines containing decongestants. Anti-depressants may enhance the effects of a stimulant, and stimulants in combination with decongestants may cause blood pressure to become dangerously high or lead to irregular heart rhythms, which in extreme cases may be fatal.

Solid dosage forms are particularly susceptible to abuse. For example, tablets oral drug delivery can be ground down into a powder. Drug addicts and abusers grind down the tablet in order to nasally inhale the drug. Addicts also grind the tablet to extract the drug into alcohol or water to make a concentrated injectable drug solution. Administration of various abused drugs in this way produces a sudden high dose of drug into the blood stream making the user euphoric. These well-known techniques for drug abuse have been used for many years with all manner of drugs.

One particularly important example of a highly addictive drug that is commonly abused by crushing (for nasal inhalation), and/or alcohol or water extraction (for intravenous injection) is Oxycodone. Oxycodone is a powerful analgesic that is available in tablet form (Oxycontin®, Purdue Pharmaceuticals) and is manufactured in 10 mg, 20 mg, 40 mg, 80 mg, and 160 mg tablet strengths. The Oxycontin® tablets are formulated as time-release tablets (about 12 hours of release), but of course crushing and grinding down the tablet destroys any controlled-release properties. It has been alleged that Oxycontin® abuse has so far resulted in at least 120 deaths nationwide (http://www.stopoxycontinaddiction-.com/oxycontin-addiction.htm). 5 mg of Oxycontin® has as much active ingredient (oxycodone) as one Percocet™. So chewing/snorting a crushed 40 mg Oxycontin® is like taking eight Percocet™ at once or a 80 mg Oxycontin® is like taking 16 Percocet™ all at once. Overdose produces small pupils, slow breathing, dizziness, weakness, seizures, the loss of consciousness, coma, and sometimes death.

The above problems present a clear and long-felt challenge to drug manufacturers to produce drug dosage forms that also allow for desirable drug release kinetics and reduced potential for abuse.

SUMMARY OF THE INVENTION

The invention relates to a dosage form comprising a formulation, the formulation comprising a drug, a HVLCM, a network former, and an optional rheology modifier. The formulation may also include a solvent. In another aspect, the invention relates to an oral dosage form comprising a formulation having a drug, wherein the formulation, upon exposure to an aqueous environment, forms a network within the formulation and an outer surface. The formulations of the invention show desirable drug-release kinetics and/or abuse deterrence characteristics.

The invention relates to a drug delivery device comprising a formulation, the formulation comprising a HVLCM, a network former and an optional rheology modifier, and, in certain embodiments also comprising a solvent. In another aspect, the invention relates to a drug delivery device comprising a formulation, wherein the formulation, upon exposure to an aqueous environment, forms a network within the formulation and an outer surface. These devices can be used to deliver any type of biologically active compound including drugs for example opioids, CNS depressants and stimulants. In a another embodiment, the invention relates to an oral dosage form comprising a formulation, the formulation comprising a HVLCM and an opioid. In a more specific embodiment, the formulation contains oxycodone, sucrose acetate isobutyrate (SAIB), cellulose acetate butyrate (CAB), isopropyl myristate (IPM) and ethyl lactate (EL).

A particular advantage of the dosage form and delivery device of the invention is that, in a particular embodiment, it provides an oral dosage form comprising a formulation having a drug, comprising one or more of an HVLCM, a network former, a rheology modifier, and a solvent, present in amounts effective to reduce the rate of extraction of the drug, for example, with water, ethanol, or other solvents, while simultaneously providing desired drug release kinetics. This reduced rate of extraction contributes to abuse deterrence and reducing risk of diversion.

SPECIFIC EMBODIMENTS OF THE INVENTION

Figure 1:
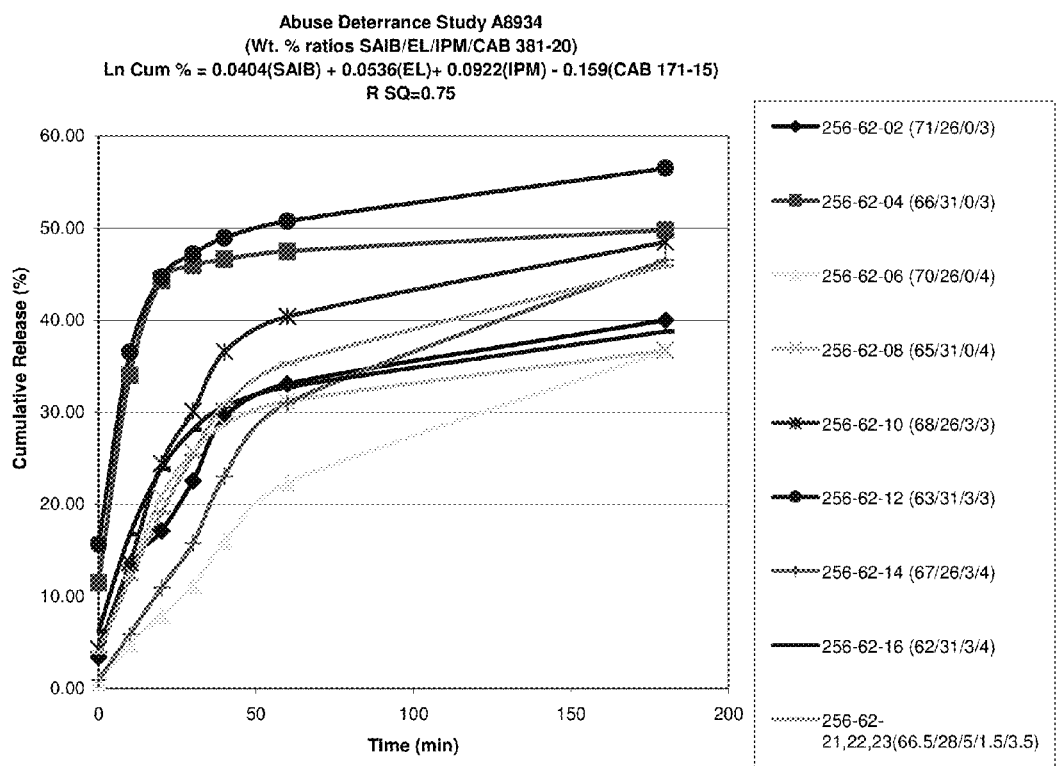
FIGS. 1-4, and 11 are graphs that show representative results from an abuse-deterrence study. The units of the graphs are relative percentage cumulative release vs. time (minutes).

Abbreviations used throughout the disclosure are as follows:
HVLCM: High Viscosity Liquid Carrier Material
SAIB: Sucrose Acetate Isobutyrate
EL: Ethyl Lactate
IM (or IPM): Isopropyl Myristate
CAB: Cellulose Acetate Butyrate
OC (or OXY): Oxycodone free base or salt A derivative of a compound refers to any molecule the structure of which is based on the structure of the original compound. The derivative may have substituted substituent groups or may have additional groups added, or may have groups removed, but it substantially shares the same core structure as the original compound. Derivatives of compounds include for example the free bases, salt, and the hydrates of such compounds.

Drug delivery device refers to a device for holding or containing and releasing a drug wherein after administration of the drug delivery device to a subject, in particular, a human subject, the drug is released from the drug delivery device into a subject. The device for holding or containment may be any type of containment device, including injectable devices (pumps etc) and ingestible devices, including a tablet, pill, capsule or formulation. Many drug delivery devices are described in *Encyclopedia of Controlled Drug Delivery* (1999), Edith Mathiowitz (Ed.), John Wiley & Sons, Inc.

Drug refers to any substance intended for use in the diagnosis, cure, mitigation, treatment, or prevention of any disease, disorder, or condition or intended to affect the structure or function of the body, other than food. It can include any beneficial agent or substance that is biologically active or meant to alter animal physiology Dosage form refers to a drug and a drug delivery device.

Formulation refers to one or more ingredients or compounds. For example, a drug formulation is any drug combined together with any pharmaceutically acceptable excipients, additives, solvents, carriers and other materials.

High Viscosity Liquid Carrier Materials (HVLCMs) refers to non-polymeric, non-water soluble liquids with a viscosity of at least 5,000 cP at 37° C. that do not crystallize neat under ambient or physiological conditions. HVLCMs may be carbohydrate-based, and may include one or more cyclic carbohydrates chemically combined with one or more carboxylic acids, such as Sucrose Acetate Isobutyrate (SAIB). HVLCMs also include nonpolymeric esters or mixed esters of one or more carboxylic acids, having a viscosity of at least 5,000 cP at 37° C., that do not crystallize neat under ambient or physiological conditions, wherein when the ester contains an alcohol moiety (e.g., glycerol). The ester may, for example comprise from about 2 to about 20 hydroxy acid moieties. Various HVLCMs used with the present drug-delivery system are described in U.S. Pat. Nos. 5,747,058; 5,968,542; and 6,413,536, all incorporated by reference hereby. The present invention may employ any HVLCM described in these patents but is not limited to any specifically described compounds.

Rheology modifier refers to a substance that possesses both a hydrophobic and a hydrophilic moiety. Rheology modifiers used with the invention generally have a logarithm of octanol-water partition coefficient of between about −7 and +15, preferably between −5 and +10, more preferable between −1 and +7. Rheology refers to the property of deformation and/or flow of a liquid, and rheology modifiers are used to modify viscosity and flow of a liquid formulation. Rheology modifiers include, for example, caprylic/capric triglyceride (Migliol 810), isopropyl myristate (IM or IPM), ethyl oleate, triethyl citrate, dimethyl phthalate, and benzyl benzoate.

Network former refers to a compound that forms a network structure when introduced into a liquid medium (such as a HVLCM). Network formers may be added to the liquid formulation (such as a HVLCM) such that, upon exposure to an aqueous environment, they form a three dimensional network within the formulation. Network formers include, e.g., cellulose acetate butyrate, carbohydrate polymers, organic acids of carbohydrate polymers and other polymers, hydrogels, as well as particles such as silicon dioxide, ion exchange resins, and/or fiberglass, that are capable of associating, aligning or congealing to form three dimensional networks in an aqueous environment.

Solvents refers to any substances that dissolve another substance (solute). Solvents may be used in an HVCLM formulation to dissolve other components such as drugs, network formers, rheology modifiers and stabilizers. Solvents may include alcohols, organic acids and their derivatives, esters of organic acids, and compounds possessing an alcohol and an organic acid residue e.g., ethyl lactate (EL) or triacacetine, dimethyl sulfoxide (DMSO), propylene carbonate, N-methylpyrrolidone (NMP), ethyl alcohol, benzyl alcohol, glycofurol.

Stabilizer refers to any substance used to inhibit or reduce degradation (e.g., chemical) of other substances with which the stabilizer is mixed. Exemplary stabilizers typically are antioxidants that prevent oxidative damage and degradation, e.g., sodium citrate, ascorbyl palmitate, vitamin A, and propyl gallate and/or reducing agents.

In situ refers to laboratory conditions simulating conditions in the GI tract of a mammal (see table 1).

Placebo refers to formulations without active drug (e.g., "a placebo solution" in Table 1).

DETAILED DESCRIPTION

Please note that the examples described herein are illustrative only and in no way limit the scope of the invention.

Dosage forms and drug-delivery devices suitable for delivery of a drug are disclosed. Certain of these devices are suitable for the oral delivery of a drug. The dosage form or device includes a formulation that includes an HVLCM and one or more of a network former, an optional rheology modifier and/or a solvent. In particular, the formulation can be loaded with a drug, and will release the drug over a period of time when in an aqueous environment, and in particular, an environment similar to that of the GI tract of a mammal. While not wishing to be bound by theory, it is believed that the network former allows the formation of a micro-network within the formulation upon exposure to an aqueous environment. This micro-network formation appears to be due, at least in part, to a phase inversion (e.g., a change in glass transition temperature, $T_g$) of the network former. The result is believed to be a skin or surface layer of precipitated network former at the interface between the dosage form and the aqueous environment of the GI tract, as well as the formation of a three-dimensional micro-network of precipitated network former within the dosage form.

Figure 5:
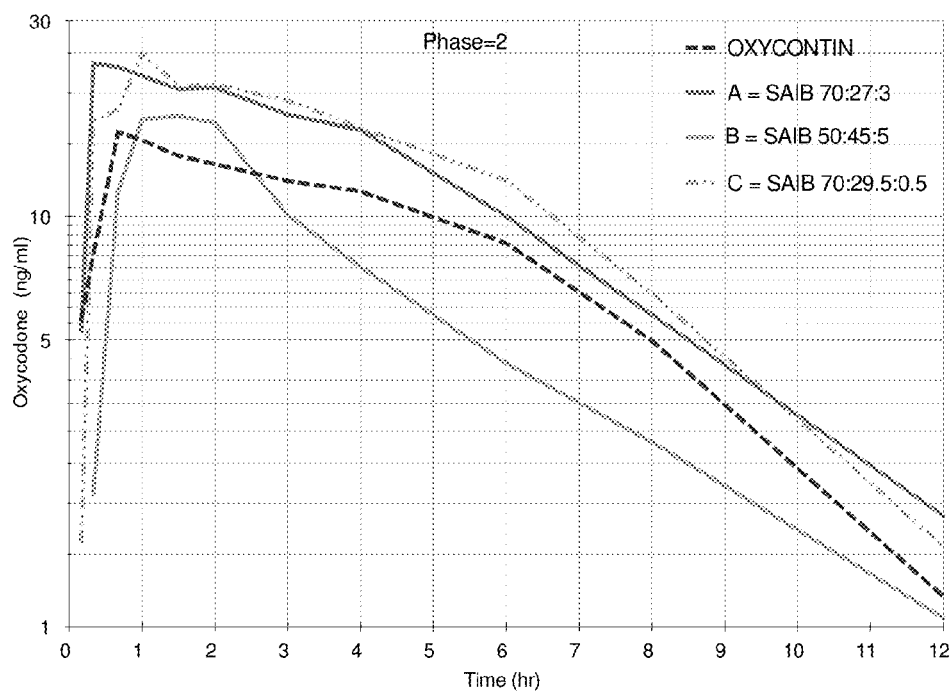
FIG. 5 is a graph from a representative dog pharmacokinetic (PK) study showing plasma concentration (ng/ml) vs. time (hr) for three SAIB soft gelcaps containing oxycodone formulations (A, B and C); compared with an Oxycontin® tablet.

Preferred dosage forms comprising drug delivery devices of the invention do not become substantially emulsified during passage through the GI tract, but substantially maintain their integrity (deformability and/or surface characteristics), while passing through the GI tract and releasing drug. While not wishing to be bound by any theory, it is believed that the formulation forms a network on the surfaces and/or in the bulk phase. The surfaces are renewed, such that the concentration gradient is maintained at the surfaces for desirable drug release kinetics. This phenomenon was observed by the inventors during the dog plasma PK study that produced the results as shown in FIG. 5. The dosage form when exiting the GI tract may retain a substantial proportion of its weight; for example, desirable dosage forms can have a weight that is no less than about 50% of the weight of the dosage form upon oral administration. This percentage weight may vary with different formulations used in dosage forms, and may be at least 60%, 70%, 80%, or even 90% of the original weight.

In preferred embodiments, the formulation comprises a HVLCM along with various additives and excipients. HVLCMs used in certain embodiments are generally hydrophobic, non-polymeric, non-water soluble liquids with a viscosity of at least 5,000 cP at 37° C. that do not crystallize neat under ambient or physiological conditions. Various HVLCMs used with the invention are described in U.S. Pat. Nos. 5,747,058; 5,968,542; and 6,413,536 and in U.S. Ser. No. 09/699,002, filed Oct. 26, 2000 and Ser. No. 10/316,441, filed Dec. 10, 2002, the entire contents of which are incorporated herein by reference. Sucrose Acetate Isobutyrate (SAIB) has been found to be a particularly suitable HVLCM for many of the applications described herein.

The dosage forms and drug delivery devices of the invention can be used to deliver any type of biologically active compound. Examples of such biologically active compounds delivered using the invention include opioids, CNS depressants and stimulants, as well as proteins, hormones, chemotherapeutic agents, anti-nausea medication, antibiotics, antivirals and other agents. One class of drug of particular interest for delivery using the system disclosed herein is opioids, which includes alfentanil, allylprodine, alphaprodine, anileridine, apomorphine, apocodeine, benzylmorphine, bezitramide, buprenorphine, butorphanol, clonitazene, codeine, cyclazocine, cyclorphen, cyprenorphine, desomorphine, dextromoramide, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, morphine, myrophine, nalbuphine, narceine, nicomorphine, norlevorphanol, normethadone, nalorphine, normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, propheptazine, promedol, profadol, properidine, propiram, propoxyphene, remifentanyl, sufentanyl, tramadol, tilidine, naltrexone, naloxone, nalmefene, methylnaltrexone, naloxone methiodide, nalorphine, naloxonazine, nalide, nalmexone, nalbuphine, nalorphine dinicotinate, naltrindole (NTI), naltrindole isothiocyanate, (NTH), naltriben (NTB), nor-binaltorphimine (nor-BNI), beta-funaltrexamine (b-FNA), BNTX, cyprodime, ICI-174,864, LY117413, MR2266, etorphine, DAMGO, CTOP, diprenorphine, naloxone benzoylhydrazone, bremazocine, ethylketocyclazocine, U50,488, U69, 593, spiradoline, DPDPE, [D-Ala2,Glu4] deltorphin, DSLET, Met-enkephalin, Leu-enkephalin, β-endorphin, dynorphin A, dynorphin B, a-neoendorphin, or an opioid having the same pentacyclic nucleus as nalmefene, naltrexone, buprenorphine, levorphanol, meptazinol, pentazocine, dezocine, or their pharmacologically effective esters or salts.

The dosage form disclosed allows for the release of drug including over a prolonged period, such as of several hours. The total period for release of drug in an amount sufficient to be an effective dosage may be greater than 20 hours, or greater than 17 hours, or greater than 15 hours, or greater than 12 hours, or greater than 10 hours, or greater than 8 hours, or greater than 6 hours, or greater than 4 hours, or greater than 2 hours, or greater than 1 hour. The amount of drug sufficient to provide an effective dosage is determined from the therapeutic range of the drug, which is determined from, for example, clinical trials, and this information is easily available to one of skill in the art.

The drug delivery device disclosed may include various components in addition to the carrier material (generally a HVLCM). The additional compounds may be present in amounts ranging from about 75 wt % to as low as about 0.01 wt % of the total formulation. These additional components may include the following types of compounds:

Solvents, e.g., ethyl lactate (EL) or triacetine, DMSO, Propylene carbonate, NMP, Ethyl alcohol, Benzyl alcohol, Glycofurol, alpha-tocoperol, Miglyol 810, isopropyl alcohol, diethyl phthalate, PEG 400, triethyl citrate, benzyl benzoate.

Network formers, e.g., cellulose acetate butyrate (CAB 171-15, CAB 381-2 and CAB 381-20, supplied by Eastman Chemicals, the characteristics of which are described in Table 2); carbohydrate polymers, organic acids of carbohydrate polymers and other polymers, hydrogels, as well as particles such as silicon dioxide, ion exchange resins, and/or fiberglass, that are capable of associating, aligning or congealing to form three dimensional networks in an aqueous environment. Other examples include cellulose acetate phthalate, ethyl cellulose, Pluronic, Eudragit, Carbomer, hydroxyl propyl methyl cellulose, cellulose acetates such as CA 381-2 and cellulose triacetate, PMMA, CAB 500-5.

Rheology modifiers, e.g., caprylic/capric triglyceride (Migliol 810), isopropyl myristate (IM or IPM), ethyl oleate, triethyl citrate, dimethyl phthalate, and benzyl benzoate.

Stabilizers, e.g., antioxidants such as sodium citrate ascorbyl palmitate, and propyl gallate and/or reducing agents. Other examples include ascorbic acid, vitamin E, sodium bisulfite, butylhydroxyl toluene, BHA, acetylcysteine, monothioglycerol, phenyl-alpha-napthylamine, lecithin, EDTA.

These and other additional compounds (discussed in greater detail below) may be altered so as to control the rate of release of a drug and/or the maximum dosing (e.g. solubility) of a drug used with the drug delivery device of the invention (Handbook of Pharmaceutical Excipients $3^{rd}$ ed., A. Kibbe, Am. Pharm. Assn., pub.).

In certain embodiments, the orally-administered, drug delivery device disclosed may be formulated so as to produce particular controlled plasma levels of drug over a particular period. This is obviously of great importance in maintaining a drug-plasma level within an appropriate therapeutic range. An appropriate therapeutic range will vary depending on the drug, but can range from femtogram/ml levels up to above microgram/mil levels for a desired period of time. For example, a single dose of a drug dosage form disclosed herein may result in maintenance of plasma levels of a drug at greater than 5 ng/ml for a period of greater than 8 hours (See FIG. 5, discussed in detail below). In other embodiments, the drug plasma level achieved using a single dose may be greater than 5 ng/ml for a period of greater than 10 hours, greater than 12 hours, greater than 14 hours, greater than 16 hours, greater than 18 hours, or greater than 20 hours. In yet other embodiments, the drug plasma level achieved using a single dose may be greater than 5 ng/ml, greater than 10 ng/ml, greater than 15 ng/ml, greater than 20 ng/ml, greater than 30 ng/ml, greater than 40 ng/ml, greater than 50 ng/ml for a period of 4, 8, 10, 12, 14, 16, 18 or 20 hours.

The maximum plasma concentration of drug may be reached at a time following administration from between 0.1 hr to about 24 hr, or from about 0.25 hr to 10 hr, or from about 0.25 hr to 8 hr, or from about 0.5 hr to 6 hr, or from about 0.5 hr to 4 hr, or from about 0.5 hr to 2 hr, or from about 0.5 hr to 1 hr. The time to maximum plasma concentration may be adjusted by adjusting various components of the drug delivery device as taught herein. Altering components alters viscosity or other rheological characteristics of the formulation and concomitantly alters rate of drug release (discussed in detail below). The rate of reduction of plasma drug concentration over time may also be adjusted by varying components of the drug delivery device. Any desired release profile may be achieved by altering components as described herein.

The plasma levels obtained may be adjusted by adjusting the formulation and other components of the drug delivery device, and desirable plasma levels will depend on the therapeutic range or its index for any particular drug. It is readily within the skill of one in the art to determine the desired therapeutic index, and in view of the current disclosure, it would be a matter of routine experimentation to adjust the various components in order to achieve the desired release characteristics for a particular drug.

Figure 7:
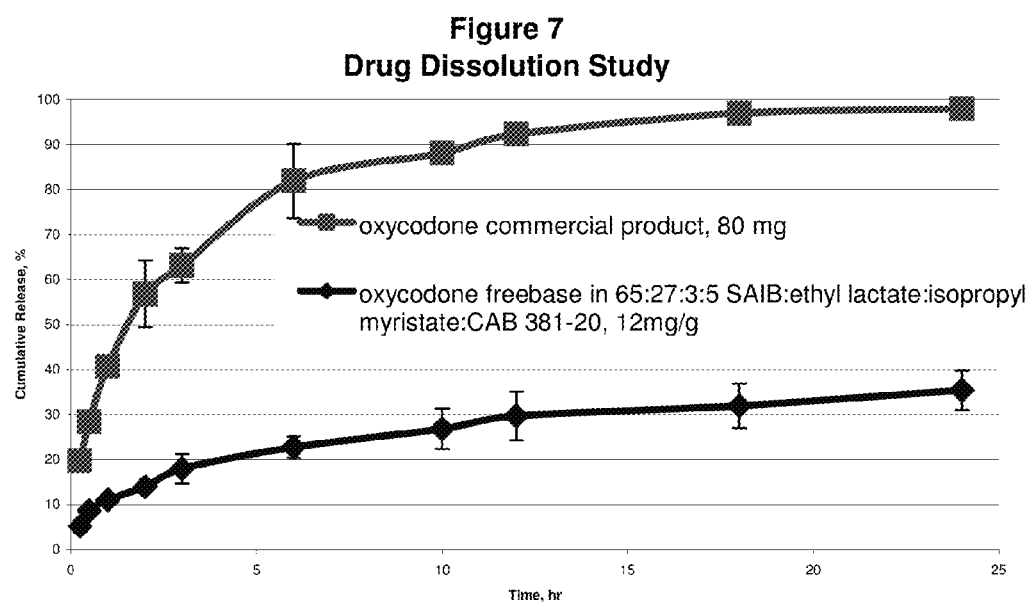
FIG. 7 is a graph showing representative dissolution results of drug in a simulated gastrointestinal environment (cumulative % release vs. time).

In certain embodiments, the release profile of drug over the release period is preferably approximately steady over time, sufficient to provide a therapeutic dose over the release period, and preferably shows a decreased burst effect when compared to a standard tablet formulation. As can be seen from FIG. 7 (discussed in more detail later), the drug delivery device of the invention can release drug (in this case, oxycodone) at an approximately steady rate over a period of at least 24 hours. The release rate is particularly steady from about 1 hr to greater than 24 hrs. This is in contrast to a commercial tablet formulation (OxyContin®) that provides substantial drug release during the first 5 hr period. In the case as shown in FIG. 7, the dosage form using the drug delivery device of the invention provides a long term in vitro release with less than 40% of drug released within 24 hours, whereas the commercial dosage form provides nearly 100% release in 24 hours. The time to 90% release of drug may be varied by varying the formulation and other device components and may be as little as 4 hours, 6 hours, 8 hours, 10, hours, 12 hours, 16 hours or 20 hours, or up to about 24 hours.

The rate of drug release from the dosage form may be varied depending on the drug used and dosage required. Release rates may be different in different parts of the GI tract, and release rates may be averaged over the time of transit through the GI tract (approximately 8-24 hrs). Typical average release rates may vary substantially. For many drugs, they may range from about 0.01 to 500 mg/hr, from 0.5 to 250 mg/hr, 0.75 to 100 mg/hr, 1.0 to 100 mg/hr, 2.0 to 100 mg/hr, 5 to 100 mg/hr, 10 to 100 mg/hr, 10 to 80 mg/hr, 20 to 50 mg/hr, or about 20 to 40 mg/hr.

Dosage regimens for the drug may be determined by the physician in accordance with standard practices. Once per day or twice per day (BID) dosing may be used to maintain a sufficient clinical effect, e.g., to maintain pain relief.

An important advantage of the dosage forms disclosed herein is that they have abuse-deterrent characteristics and/or reduced risk of diversion. The dosage form, and the formulation contained therein is not susceptible to crushing, powdering or extraction using ethanol or water. Specifically, HVLCM is a viscous liquid, and so formulations containing HVLCMs avoid the possibility of crushing for the purpose of inhalation. Additionally, the formulation of the invention has the characteristic of being resistant to drug extraction using ethanol or water, when compared to a tablet formulation of a drug.

In certain preferred embodiments, the drug-delivery device is composed of a drug formulation encapsulated within an enclosure or capsule, preferably biodegradable, such as a capsule or a gelatin capsule ("gelcap"), wherein the capsule is made of a substance that degrades or otherwise dissociates when exposed to conditions present in the gastro-intestinal tract of a mammal. Capsules and gelcaps are well known in drug delivery technology and one of skill could select such a capsule as appropriate for delivery of a particular drug. Once the capsule has dissolved or dissociated from the formulation, the formulation of the invention generally remains intact, especially for hydrophobic formulations, and passes through the GI tract without emulsification or fragmentation.

In certain more specific embodiments the invention encompasses an oral dosage form comprising a formulation contained within a biodegradable capsule, wherein the formulation comprises a drug and a HVLCM, and wherein the capsule is made of a substance that degrades when exposed to conditions present in the gastro-intestinal tract of a mammal. In certain embodiments the capsule comprises gelatin or synthetic polymers such as hydroxyl ethyl cellulose and hydroxyl propylmethyl cellulose. Gelcaps can be of the hard or soft variety. Gelatin capsules are well suited for delivering liquid formulations such as vitamin E and cod-liver oil. Gelatin capsules are stable in storage, but once in the acid environment of the stomach (low pH less than about pH 4-5), the gelcap dissolves over a 10-15 minute period. In certain embodiments, the drug delivery device further comprises at least one component selected from the group consisting of: Ethyl Lactate, Triacetin, Propylene Carbonate, Glycofurol, Triethyl Oleate, Isopropyl Myristate, Cellulose Acetate Butyrate, and derivatives thereof.

Figure 6:
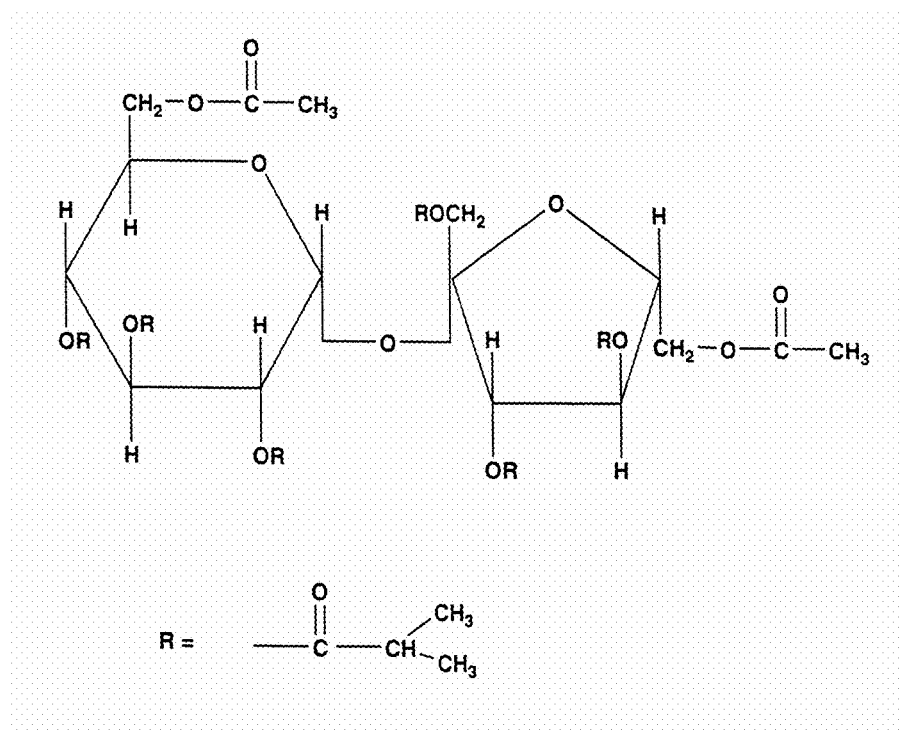
FIG. 6 is a chemical schematic showing the structure of SAIB, which is a hydrophobic, fully esterified sucrose derivative, at a nominal ratio of six isobutyrates to two acetates.

Certain preferred embodiments of the orally-administered, drug-delivery device of the invention comprise Sucrose Acetate Isobutyrate (SAIB) as the HVLCM carrier material. SAIB is a non-polymeric highly viscous liquid at temperatures ranging from −80° C. to over 100 C, it is a fully esterified sucrose derivative, at a nominal ratio of six isobutyrates to two acetates (FIG. 6). It is manufactured by Eastman Chemical Company as a mixed ester, and the resulting mixture does not crystallize but exists as a very viscous liquid. It is a hydrophobic, non-crystalline, low molecular weight molecule that is water insoluble and has a viscosity that varies with temperature. For example, pure SAIB exhibits the viscosity of approximately 2 million centipoise (cP) at room temperature and approximately 600 cP at 80 C. SAIB has unique solution-viscosity relationship in that the SAIB solutions in a number of organic solvents is significantly lower than these viscosity values for the pure SAIB and therefore the SAIB-organic solvent solutions render themselves capable of processing using conventional equipment such as mixers, liquid pumps and gelcap production machines. SAIB also has applications in drug formulation and delivery, for example as described in U.S. Pat. Nos. 5,747,058, 5,968,542, 6,413,536, 6,498,153, all incorporated by reference herein. In the present invention, SAIB may be used as the HVLCM and may be present in quantities that vary significantly. For example, quantities of at least about 50, 60, 70, 80, 90, 95, 97, 98, 99, 99.5 or 99.9 wt % can be used. Various formulations containing SAIB are discussed in the examples.

In addition, certain embodiments of the drug delivery device as disclosed allow the oral delivery of compounds, such as proteins, that would not normally be considered effectively orally administrable because administration in conventional oral compositions would likely result in the breakdown of the active agent by stomach acids or enzymes.

One embodiment of the invention relates to opioid dosage forms suitable for oral administration, including those that provide desirable drug release kinetics and/or limit the likelihood that diversion of the opioids in the dosage forms could occur by patients or others. In this embodiment, the opioids can be dissolved or dispersed in the formulation component of the invention, which can be simply a HVLCM. Suitable opioid compounds deliverable according to the invention include, for example, those generally used as pain relievers, narcotics and/or anesthetics, and include alfentanil, allylprodine, alphaprodine, anileridine, apomorphine, apocodeine, benzylmorphine, bezitramide, buprenorphine, butorphanol, clonitazene, codeine, cyclazocine, cyclorphen, cyprenorphine, desomorphine, dextromoramide, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, morphine, myrophine, nalbuphine, narceine, nicomorphine, norlevorphanol, normethadone, nalorphine, normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, propheptazine, promedol, profadol, properidine, propiram, propoxyphene, remifentanyl, sufentanyl, tramadol, tilidine, naltrexone, naloxone, nalmefene, methylnaltrexone, naloxone methiodide, nalorphine, naloxonazine, nalide, nalmexone, nalbuphine, nalorphine dinicotinate, naltrindole (NTI), naltrindole isothiocyanate, (NTII), naltriben (NTB), nor-binaltorphimine (nor-BNI), beta-funaltrexamine (b-FNA), BNTX, cyprodime, ICI-174,864, LY117413, MR2266, etorphine, DAMGO, CTOP, diprenorphine, naloxone benzoylhydrazone, bremazocine, ethylketocyclazocine, U50,488, U69,593, spiradoline, DPDPE, [D-Ala2,Glu4] deltorphin, DSLET, Met-enkephalin, Leu-enkephalin, β-endorphin, dynorphin A, dynorphin B, a-neoendorphin, or an opioid having the same pentacyclic nucleus as nalmefene, naltrexone, buprenorphine, levorphanol, meptazinol, pentazocine, dezocine, or their pharmacologically effective esters or salts.

The oral dosage forms of these opioids may be prepared by simply mixing a HVLCM, a rheology modifier, a network former, the active agent, a solvent and any additives, and introducing the resulting mixture into a gelatin capsule. Alternative formulations may include emulsifying the mixture in water, and introducing this emulsion into the gelatin capsule, or using one or more of the techniques described herein to produce the dosage form.

In another embodiment of the invention, the HVLCM can be used as the continuous phase in a dispersion of particulate biologically active agent. For example, SAIB, which is extremely viscous, can be used to suspend particles of lyophilized protein, microparticles, microspheres, or microcapsules of drugs, for example, biologically active agents, to produce suspension formulations. Concentrations of the active agent in the suspension formulation are analogous to those disclosed above. The resulting suspension formulation has excellent storage stability.

Preferred embodiments of this invention provide an effective, user-friendly and inexpensive ingestible oral dosage form that allows sustained drug release, with favourable drug-release kinetics, during transit through the gastrointestinal tract, and is less subject to abuse than current tablet and capsule dosage forms. The invention encompasses a controlled release oral drug delivery device. One drug delivery device of this invention encompasses a SAIB-drug formulation which may be enclosed in a gelatin capsule suitable for oral delivery. Different embodiments may use some or all of the following additional components in the formulation to effect appropriate drug delivery kinetics: Solvents, e.g., ethyl lactate (EL) or triacacetine, DMSO, Propylene carbonate, NMP, Ethyl alcohol, Benzyl alcohol, Glycofurol. Network formers, e.g., cellulose acetate butyrate (CAB 171-15, CAB 381-2 and CAB 381-20 supplied by Eastman Chemicals). Rheology modifiers, e.g., caprylic/capric triglyceride (Migliol 810) and other plasticizers such as isopropyl myristate (IM or IPM), triethyl citrate, dimethyl phthalate, and ethyl oleate, benzyl benzoate. Stabilizers, e.g., antioxidants such as sodium citrate ascorbyl palmitate, and propyl gallate. A specific example of a formulation for use in the drug delivery device of the invention contains oxycodone free base and/or hydrochloride salt, SAIB, ethyl lactate, isopropyl myristate, and CAB. An exemplary embodiment, used by the inventors to produce data disclosed herein, is formulated as follows: oxycodone free base 10 mg per gelcap, SAIB 65%, ethyl lactate 27%, isopropyl myristate 3% and CAB 381-20 5% (all percentages are weight percent). This formulation is placed into a soft gelcap.

The dosage form of the invention may comprise one or more drugs. The amount of drug(s) and percentages of components in the formulation may vary. Typical average amounts may vary substantially. For many drugs, they may range from about 0.1 mg to 1000 mg, or from about 1 mg to 500 mg, or from about 2 mg to 250 mg, or from about 2 mg to 250 mg, or from about 2 mg to 150 mg, or from about 5 mg to 100 mg, or from about 5 mg to 50 mg. The precise amount of drug desired can be determined by routine methods well known to pharmacological arts, and will depend on the type of drug, and the pharmacokinetics and pharmacodynamics of that drug.

The percent weight of HVLCMs may vary depending on the characteristics of the dosage form desired, and may be for example include from about 30%, 40%, 50%, 60%, 70%, 80%, 90%, 95%, 99%, 99.5%, to about 100%. Exemplary formulations disclosed herein contain 99%, 71%, 70%, 65%, 63%, 61.6%, 59%, 50%, 40%, 30%, 20% or even lesser amounts of SAIB. Variation in SAIB content may be made to alter viscosity or other rheological properties of the formulation and to alter the rate at which drug is delivered. Using the information presented here, ones skilled in the art could alter the SAIB content of the formulation to suit various drugs of differing hydrophobicity or hydrophilicity, and determine the optimum rate of drug release from the formulation.

The dosage form of the invention may comprise one or more solvents. The percent weight of solvent(s) (such as EL) may vary depending on the characteristics of the dosage form desired, and may be for example from about 0% to about 60%, or from about 20% to about 50%, or from about 25% to about 48%. Exemplary formulations disclosed herein include those with 48%, 45%, 36.3%, 31.4%, 29.5%, 29%, 27%, and 23% EL. Again, using the information presented herein, ones skilled in the art could adjust the percent of solvent and determine the optimum amount required for delivery of a particular drug. More than one solvent can be used in a SAIB formulation.

The dosage form of the invention may comprise one or more rheology modifiers. The percent weight of rheology modifier(s) may vary depending on the characteristics of the dosage form desired, and may be for example vary from about 0.1% to about 10%, or from about 0.5% to about 5%, or from about 1% to about 4%. Exemplary formulations disclosed herein include those with 3.5%, 3%, and 1%, and 0%, IM. Using the information presented herein, ones skilled in the art could adjust the percent of formulation viscosity or other rheology modifier and determine the optimum amount required for delivery of a particular drug. More than one rheology modifier can be used in a SAIB formulation.

The percent weight of network former(s) may vary depending on the characteristics of the dosage form desired, and may be for example from about 0% to about 20%, or from about 0.1% to about 10%, or from about 0.5% to about 9%, or from about 1% to about 8.6%. Exemplary formulations disclosed herein include those with 8.6%, 7.8%, 5%, 4.5%, 3%, 2.1%, 2%, 1%, 0.5% and 0% CAB. Different types of CAB (e.g., CAB 381-20, CAB 381-2, and CAB 171-15) may be used to affect desired drug release characteristics. Again, using the information presented herein, ones skilled in the art could adjust the percent of the network former and determine the optimum amount required for delivery of a particular drug. More than one network former can be used in a SAIB formulation.

The formulations of the invention may use network formers such as cellulose acetate butyrate of varying acetyl and butyryl content such as CAB 381-20, CAB 381-2 and CAB 171-15. CAB allows the in-situ formation of a micro-network within the SAIB-drug formulation. Although not wishing to be bound by theory, it appears that the mechanism of micro-network formation appears in part to be due to phase inversion (e.g., change in $T_g$) of network formers. That is to say, when SAIB formulations containing the CAB type of network former (for example CAB 381-20) are exposed to or immersed in aqueous environments such as the mammalian gastrointestinal (GI) tract, previously dissolved network formers in SAIB formulations will precipitate as a result of migration of water and other biologically available fluid components, which will result in polymer precipitation process and yield polymeric networks within the drug delivery device. The formation of micro-network will begin at the surface of the formulation mass and the polymeric network will gradually propagate toward the center of the formulation mass, resulting in a progressive increase in SAIB formulation viscosity in situ.

In conjunction with the network formers, solvents such as ethyl lactate, and rheology modifiers such as isopropyl myristate, when formulated into SAIB, appear to confer a number of unexpected characteristics to the HVLCM formulations. The characteristics include rheological (e.g., viscosity) characteristics, drug release kinetics, and abuse-deterrence characteristics.

It was discovered that the drug release rates in the early and/or late time periods increased with increasing content of the network forming polymers in the presence of varying concentration of ethyl lactate and isopropyl myristate. However, the effects of ethyl lactate (EL) varied, and, for example, during early time periods (0-6 hours) increasing EL concentration increased the drug release rate while in late time periods (from 6-24 hours), the drug release rate decreased with increasing concentration of EL. Also, notably, drug extractability from SAIB drug formulations using ethanol solutions consistently decreased with addition of CAB polymers regardless of the concentrations of ethyl lactate and isopropyl myristate.

Also, it was discovered that addition of CAB polymer in SAIB formulations consistently raised the viscosity of the SAIB formulations before and after immersion in 37° C. aqueous media. However, the addition of other components i.e., ethyl lactate and isopropyl myristate was discovered to decrease viscosity before water immersion, but increase viscosity following the immersion in water. These observations are highly unexpected based on a previous understanding of solvents and plasticizers in SAIB drug formulations.

The present invention allows for adjustment of a number of performance characteristics of HVLCM formulations by adjusting the ratios of individual formulation ingredients such as solvents, rheology modifiers and network formers, including optimization thereof. The current invention also discloses new and surprising interrelationships between the formulation ingredients, which resulted in unique and non-obvious formulation rheology, drug release kinetics, rate and extent of drug absorption in vivo, and/or desirable abuse deterrence characteristics including reduced drug extractability, for example, by alcoholic or aqueous solutions.

The invention provides a dosage form that reduces or eliminates drug abuse wherein the route of abuse may include, for example snortable, inhalable, intravenous, sublingual, bucal, subcutaneous, percutaneous, vaginal, rectal or intraocular means. The present dosage form has several important abuse-deterrent characteristics: it is non-crushable (for abusive nasal inhalation) and it provides a formulation, e.g., that makes alcohol-extraction or water-extraction of the drug very difficult, producing a poor drug yield.

The dosage forms of the invention show unexpectedly favourable drug-release kinetics. For example, the SAIB/ Oxycodone formulation provides improved pharmacokinetic parameters such as shorter Tmax, greater and/or equivalent Cmax and AUC (area under curve) and improved bioavailability of the drug when compared with a currently marketed formulation (e.g., OxyContin®).

Another unexpectedly favourable property of the formulation of the invention is that the formulation bolus appears to stay substantially intact as it passes through the GI tract. For example, the SAIB-based formulation is released from the gelatin capsule when the capsule is dissolved, but the formulation bolus itself is not emulsified as it passes through the stomach, gut or colon despite being, it is believed, kneaded or deformed by GI motility (peristaltic motion). While not wishing to be bound by theory, it is believed that surface renewal occurs by relatively constant renewal of surface drug concentration by diffusion of the drug from the interior of the bolus, and by deformation and refolding of the surface, or by some combination of these mechanisms.

In a particular embodiment, the invention provides an oral dosage form comprising a formulation contained within a biodegradable capsule, wherein the formulation comprises a drug, a HVLCM, a rheology modifier, a network former and a solvent, and wherein the capsule is made of a substance that degrades when exposed to conditions present in the gastro-intestinal tract of a mammal. In preferred embodiments, the HVLCM can be SAIB, and the capsule can be made from gelatin or synthetic polymers. In particular embodiments the drug may be an opioid such as oxycodone. The drug-release kinetics of dosage forms incorporating various formulations can be seen to be both unexpected and favorable for delivery of drugs such as oxycodone.

Preparation of Formulations

A method for preparation of an exemplary formulation of the invention, using SAIB as the HVLCM, is presented. Other SAIB formulations can be prepared by varying this method. The ratios refer to weight percent ratios for SAIB/ Ethyl lactate/Isopropyl Myristate/CAB 381-20, respectively.

A formulation comprising SAIB/EL/IPM/CAB (65:27:3: 5) was made as follows:

An appropriate amount ethyl lactate was placed in a beaker; while stirring slowly CAB and IPM were added (stir bar on stir plate); allowed to go completely into solution (stir bar on stir plate)—resulting mixture was left at 37° C. for 3 days; hot (80° C.) SAIB (shake in hand, then place on stir plate) was added—65:27:3:5 mixture left over a period of about 48 hrs at 37° C.; the mixture was heated to 70° C. for ~2 hours and homogenized with 20 mm probe at about 4000 rpm for 20-30 seconds; oxycodone-base was added (at 9 mg/g) and the mixture heated to 70° C. for 1 hr, then left overnight. The mixture was reheated to 70° C. to fill soft gelcaps using a hypodermic needle and matching syringe.

Formulations, Viscosity and Dissolution (Table 1)

Table 1 displays viscosity and dissolution data for various formulations. Viscosity values were determined at 26° C. and 37° C. (+/−0.1 to 0.3° C.) using Brookfield Digital Rheometer Models LV DV III and HBDV and CPE 52 cone (n=1 ea). The content of oxycodone ranged from 9 to 12 mg per gelcap in SAIB formulations (lot#X03502 contains only SAIB and oxycodone).

In addition to the compositions of SAIB formulations, Table 1 also shows viscosity at 37° C. for the formulations, both before and after immersion in 37° C. water for 6 hours (the column marked "placebo—$H_2O$" refers to the viscosity of the solution before immersion in water, and the column marked "placebo+$H_2O$" refers to the viscosity of the solution following immersion in water). The conditions of 37° C. and water immersion were intended to simulate in vivo conditions.

Table 1 also shows cumulative amount of oxycodone released (mg) during two separate periods. One period is for 0 to 6 hours, and the other for 6 to 24 hours.

Information in Table 1 was analyzed and the following semi-empirical equations were derived (see equations 1-3). Equations 1-3 were derived from the information in Table 1 for SAIB oxycodone gelcap formulations X03511 to X03518 (8 different formulations).

Equation 1 demonstrates that the drug dissolution rate from time intervals 0-6 hours increases with the increasing concentrations of EL, IPM and CAB polymers (statistical confidence is high, r=0.9).

Equation 2 shows that the drug dissolution rate from 6-24 hours increases with increasing IPM and CAB but decreases with increasing EL.

Equation 3 shows that the drug dissolution rate from 0 to 24 hours increases with the increasing EL, IPM and CAB.

The results embodied in the equations 1-3 are unexpected. One would have expected that increased CAB would decrease the dissolution rate. Instead increasing CAB appears to increase dissolution rate in the presence of EL and IPM. In addition, the role of EL changes depending on the time intervals of interest.

Equations 4-5 were calculated using formulation viscosity values before immersion in 37° C. water for 6 hours. As can be seen in equations 4-5, the correlation coefficient is excellent (r2=0.93 to 0.96). Both equations predict that viscosity will increase with increasing CAB while the viscosity will decrease with increasing EL and IPM. Based on the theories of solution rheology, this was expected.

Equations 6-7 were derived from the formulation viscosity values following immersion in water at 37° C. for 5 hours. As can be seen in these equations, as expected, increasing CAB increases viscosity following immersion in water. However, equation 6 and 7 both predict that increasing EL increases the immersion viscosity. This is unexpected. One would expect that the effect of increasing EL on immersion viscosity would be to decrease viscosity.

Table 1 displays data for the SAIB-oxycodone formulation X03502. X03502 did not contain any formulation ingredients (pure SAIB), but it did deliver a significant amount of oxycodone during the dissolution testing (0.42 mg over 0-6 hours and 0.65 mg over 6-24 hours). As can be seen by the in situ viscosity data (51,200 cP), which is significantly reduced in situ, it released oxycodone at a low rate but with a good rate control mechanism.

Table 1 also shows a number of other interesting formulations. For example X03503 (SAIB/IPM 99/1), which shows a significant rheology modification effect of 1% IPM, showed higher drug delivery rate compared with pure SAIB formulation.

In addition, table 1 presents SAIB formulations containing CAB 171-15. As can be seen in formulations X03505 to X03508 viscosity before and after immersion in water are quite significantly different from those formulations containing CAB 381-20BP. As a result SAIB oxycodone formulations containing CAB 171-15 exhibited significantly different release kinetics of oxycodone from those containing equivalent weight percent of CAB 381-20.

Below are the semi-empirical equations that were deduced from the dissolution experiment data. The equations can be used to calculate Oxycodone free base dissolution and extraction, and viscosity of placebo SAIB solutions before and after immersion in 37° C. Water for 5 hours.

1. Dissolution of Drug with Varying Wt % of Components

Cumulative drug dissolution was measured as functions of weight percent of EL, IPM and CAB 381-20BP. Eight SAIB-Oxycodone formulations with corresponding in vitro dissolution data are shown. Formulations were used in non GLP and GLP dog PK studies. Lots X03511 to X03518 (n=8).

For the following equations Y=cumulative amounts of drug dissolved (mg) or extracted (wt. %), and x1, x2 and x3 are the weight percents of EL, IPM and CAB 381-20BP, respectively.

a. Time interval from 0 to 6 hrs.

$$\frac{1}{Y1} = 3.02 - 0.15\sqrt{x1} - 0.5\sqrt{x2} - 0.37\sqrt{x3} : r^2 = 0.9 \quad \text{(equation 1)}$$

b. Time interval from 6-24 hrs.

$$\frac{1}{Y2} = 1.59 + 0.054\sqrt{x1} - 0.355\sqrt{x2} - 0.41\sqrt{x3} : r^2 = 0.95 \quad \text{(equation 2)}$$

c. Time interval from 0-24 hrs.

$$\frac{1}{Y3} = 1.05 - 0.002\sqrt{x1} - 0.21(\sqrt{x2} + \sqrt{x3}) : r^2 = 0.93 \quad \text{(equation 3)}$$

2. Viscosity of SAIB Placebo Solutions at 37° C., Before and after Immersion in Water.

(a) For SAIB Placebo Solutions Containing CAB 381-20BP (n=13) Before Immersion in Water at 37° C.:

$$Z = 3359.02 - 192.26x1 - 227.88x2 + 1240.29x3 :: r^2 = 0.93 \quad \text{(equation 4)}$$

Alternative Correlation $$\text{Ln } Z = 8.47 - 0.1x1 - 0.137x2 + 0.585x3 :: r^2 = 0.96 \quad \text{(equation 5)}$$

(b) For SAIB Placebo Solutions Containing CAB 381-20BP (n=13) After Immersion in Water @37° C. for 5 hours:

$$\text{Ln } Z1 = 3.8 + 0.056x1 - 0.00911x2 + 1.02x3 :: r^2 = 0.96 \quad \text{(equation 6)}$$

Alternative Correlation is $$Z1 = -42327.04 + 292.95x1 + 405.64x2 + 12173.84x3 :: r^2 = 0.8 \quad \text{(equation 7)}$$

Where Z and Z1 are the viscosity (cP) of SAIB placebo solutions before and after immersion in 37° C. water for 5 hours.

The above equations and equation 8, given below, derived with respect to an exemplary drug (oxycodone) allow one to formulate dosage forms in which the abuse deterrence and drug release kinetics, as well as other characteristics, can be varied and optimized to any desired extent. Similar equations can be developed with respect to other exemplary drugs.

TABLE 1

Rheological Characteristics and In Vitro Drug Release Attributes of SAIB Oxycodone Formulations

| Lot # | Composition (wt %) | Viscosity (cP) at 37° C. Placebo −H20 | Viscosity (cP) at 37° C. Placebo +H20 | Dissolution Attributes (mg of drug released over 0-6 and 6-24 hr) Σ 0-6 hr (mg) | Dissolution Attributes (mg of drug released over 0-6 and 6-24 hr) Σ 6-24 hr (mg) |
|---|---|---|---|---|---|
| X03502 | SAIB (100) | 137,000 | 51,200 | 0.42 | 0.65 |
| X03503 | SAIB/IPM (99/1) | 79,773 | 33,338 | 0.63 | 0.78 |
| X03504 | SAIB/EL/CAB 171-20 (50/48/2) | | | | |
| X03505 | SAIB/EL/CAB 171-15 (50/45/5) | 2,046 | 1.14 × 10E(6) | 2.82 | 3.53 |
| X03506 | SAIB/EL/CAB 171-15 (70/27/3) | 1,618-2,670 | 5,270-9,380 | 1.09/1.45 | 2.33/2.27 |
| X03507 | SAIB/EL/CAB 170-15 (61.6/36.3/2.1) | 325 | — | | |
| X03508 | SAIB/EL/CAB 171-15 (70/29.5/0.5) | 48 | 262 | 1.21 | 2.76 |
| X03511 | SAIB/EL/IMP/CAB 381-20 BP (59/31.4/1/8.6) | 6,296 | 120e3 | 1.7 | 3.1 |
| X03512 | SAIB/EL/IMP/CAB 381-20BP (59.8/31.4/1/7.8) | 35,720 | 346,000 | 1.42 | 2.4 |
| X03513 | SAIB/EL/IPM/CAB 381-20 BP (71/23/1/5) | 3,274 | 4,092 | 1.02 | 1.74 |
| X03514 | SAIB/EL/IPM/CAB 381-20BP (65/27/3.5/4.5) | 2,892 | 14,349 | 1.61 | 2.83 |
| X03515 | SAIB/EL/IPM/CAB 381-20BP (65/27/3/5) | 4,040-7,010 | 31,221-30,427 | 1.7 | 2.74 |
| X03516 | SAIB/EL/IPM/CAB 381-20BP (63/29/3/5) | 2,920 | 38,000 | 2.11 | 3.1 |
| X03517 | SAIB/EL/IPM/CAB 381-20BP (63/29/3.5/4.5) | 875 | 5,300 | 1.97 | 2.84 |
| X03518 | SAIB/EL/IPM/CAB 381-20BP (65/27/3/5) | 4,040-7,010 | 31.221-36,427 | 2 | 3.1 |
| X03520 | SAIB/EL/CAB 171-15 (70/27/3) | 1,618-2,670 | 5,270-9,380 | 1.64 | 2.5 |

TABLE 2

Exemplary CABs

| CAB types (supplied by Eastman Chemicals) | Butyryl Content (%) | Acetyl Content (%) | Hydroxyl Content (%) | Melting Point (° C.) | Glass Tran. Temp (° C.) | Molecular Wt (no. avg) |
|---|---|---|---|---|---|---|
| 171-15 | 17 | 29.5 | 1.5 | 127-240 | NA | NA |
| 381-2 | 36-38 | 13.5-14.5 | 1.3-1.7 | 171-185 | 130-133 | 40000 |
| 381-20 | 36 | 15.5 | 0.8 | 185-196 | 128 | 66000-83000 |

Measurement of Drug Dissolution Rates in Low pH Solution (FIG. 7)

One soft gelcap containing one of several SAIB-oxycodone formulations was placed in a standard glass beaker with a stirrer mechanism (as defined by United States Pharmacopia Apparatus II; VK 7000 USP II Dissolution Tester). 900 ml of 0.1N HCL solution at 37° C. was placed in the beaker and the solution was stirred at 50 rpm for 2 hours. During this period, the gelcap dissolved and the SAIB drug formulation was exposed to the low pH solution, and oxycodone dissolution begins. A number of 1 ml samples were taken and oxycodone concentration determined by HPLC (Perkin Elmer Series 200 LC Pump, or equivalent; UV detector, Perkin Elmer Diode Array Detector 235C, or equivalent). Following the initial dissolution step, the content of the beaker was modified to adjust pH from 1 to 6.8 by adding sodium phosphate buffer. Temperature was maintained at 37° C., and dissolution of drug continued for additional 22 hours. Additional samples of 1 ml were taken at various time points and oxycodone concentration determined by HPLC. The cumulative percentage of oxycodone dissolved into the media was calculated for each time interval and a graph drawn (FIG. 7).

FIG. 7 show the data obtained from a drug dissolution experiment. The graph shows the data for a SAIB-drug formulation in a soft gelcap (square data points) compared with a commercial oxycodone tablet (OxyContin®) (diamond data points) that was used as a reference. The y-axis represents cumulative percent of oxycodone released and the x-axis represents time (hrs).

The SAIB oxycodone formulation of FIG. 7 contained the following weight percents of ingredients: oxycodone free base 10 mg per gelcap, SAIB 65%, ethyl lactate 27%, isopropyl myristate 3% and CAB 381-20 5%. The commercial oxycodone product contained 80 mg of oxycodone. A number of other SAIB oxycodone gelcap formulations were tested for drug dissolution and results are given in Table 1.

It is apparent from FIG. 7 that the commercial oxycodone tablet showed a large initial burst of oxycodone release with nearly 50% being delivered within the first hour, and 80% delivered within six hours. The drug release following the burst was slow as compared with the initial burst. On the other hand, the SAIB oxycodone formulation showed no burst effect and displayed a more controlled and sustained release of the drug over the entire testing period.

Extraction of Drug into Ethanol

An important feature of the invention is that formulations can be made such that extraction of drug from the formulations using traditional ethanol extraction (traditionally used by drug abusers) is much less efficient than it is for the tablet and capsule formulations of the prior art.

FIGS. 1-4 and 11 are graphs that show results from an abuse-deterrence study. The aim was to determine the amount of oxycodone that could be extracted from a dosage form comprising a SAIB/oxycodone formulation in a soft gelcap using simple alcohol extraction, as used by drug abusers. The units of the graphs are percentage cumulative release vs. time (mins).

The method used to produce data for the abuse-deterrence study was as follows. Each soft gelcap was filled with 0.75 ml of formulation and was placed in 18 ml of 0.1N HCL in a 60-mL amber bottle and shaken at 240 RPM on an orbital shaker for 30 minutes. After 30 minutes, 12 ml of 200° (200 proof) ethanol was added to each bottle. The solutions were swirled by hand and a 1-ml sample was sampled from each bottle at T=0. The solutions were placed back in the orbital shaker for further shaking at 240 RPM. 1 ml samples were taken after 10, 20, 30, 40, 60 and 180 minutes of further shaking from each bottle. The results were graphed on a linear scale of cumulative release (%) vs. Time (mins).

FIG. 1 shows percentage cumulative amounts of drug extracted in percentage of initial drug loading in SAIB formulations vs. time (mins) for 9 formulations. Each formulation contains 12 mg/ml oxycodone. The formulation ID numbers and formulations component ratios are shown in the key. The ratios (weight percent) of each ingredient correspond to: SAIB:EL:IM:CAB.

From the data presented in FIG. 1, it can be seen that all ingredients and their ratios affect the extractability of drug. Using a regression analysis, the following empirical equation relating cumulative percent of drug extracted as a function of weight percent of each ingredient.

$$\text{Ln Cum \%} = 4.04 + 0.0132\, x1 + 0.0518\, x2 - 0.1994\, x3; r^2 = 0.75 \quad \text{(equation 8)}$$

where Cum % indicates the cumulative percent of drug extracted over the entire time interval, and x1, x2 and x3 are the weight percents of EL, IPM and CAB 381-20. As can be seen, the weight percent of drug that was extracted by the above described alcoholic solution decreased with increasing CAB 381-20 (see formulations 256-62-02, 256-62-04, 256-62-06 and 256-62-08). However, it was not obvious that the addition of well known rheology modifier, IPM, when added to the formulations containing 4 wt. % of CAB 381-20, did not affect the alcohol extraction of the drug as demonstrated by Formulation 256-62-16. This is contrary to a common sense in the art of pharmaceutical formulations. That is IPM, which is a rheology modifier of SAIB, would have been predicted to loosened up the SAIB formulations and facilitated the drug extraction but it did not. It was also discovered that when the CAB content was 3 wt. % as in formulation 256-62-12, addition of 3 wt. % of IPM increased significantly the drug extractability by alcohol solution versus the formulations that did not contain IPM such as formulation 256-62-04. It was concluded therefore, that low drug extractability from SAIB formulations by alcohol can be brought about not only due to optimum weight percent of CAB but also due to an optimum ratio between CAB and IPM.

Figure 2:
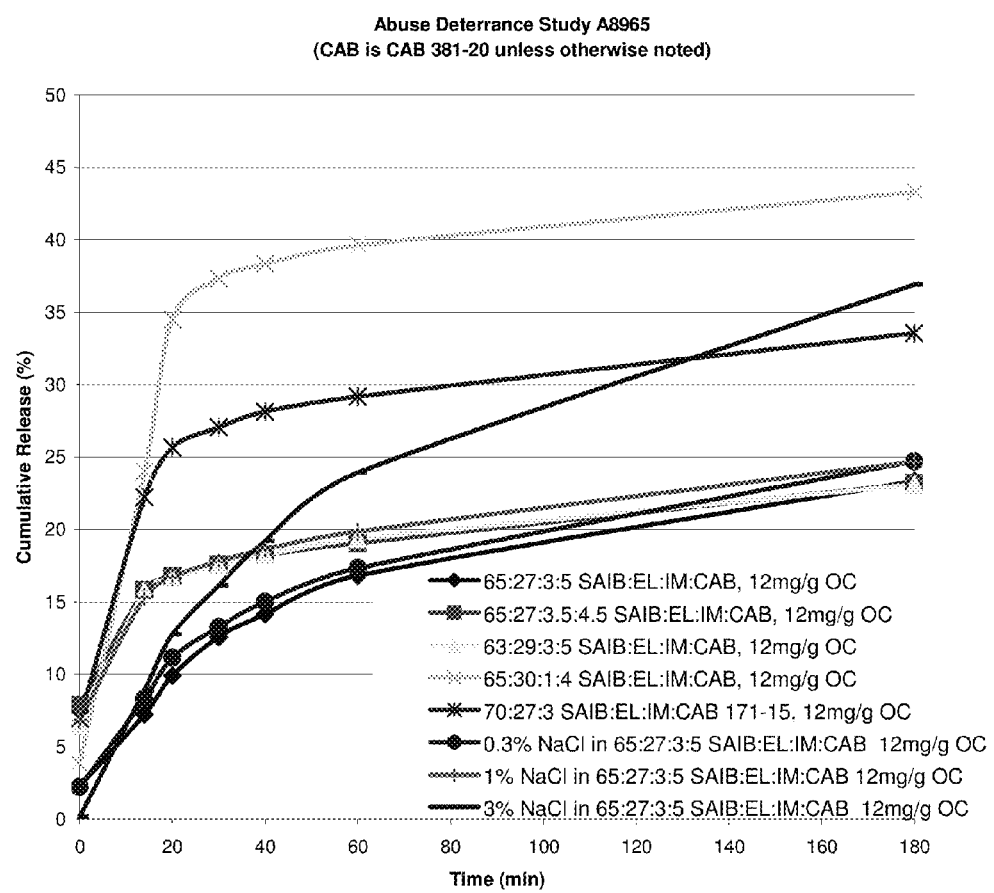

FIG. 2 shows cumulative percent of oxycodone free base extracted by alcohol vs. time (mins) for 4 formulations. Each formulation was filled into soft gelcaps. Each gelcap contained 12 mg/ml oxycodone free base.

In this experiment the effects of different ratios of IPM to CAB were evaluated for drug extractability from SAIB formulations by alcohol. The ratio varied from 0.25 to 0.78. For the given range of ratios, it was discovered unexpectedly that increasing contents of ethyl lactate, isopropyl myristate and CAB in concert reduced the drug extractability by alcoholic solution. From this experiment, it was discovered that IPM and CAB were quantitatively reciprocally interchangeable, such that increasing one component and decreasing the other by the same wt % resulted in a formulation with unchanging rheological properties. This is particularly surprising discovery in light of the fact that IPM is a rheology modifier that makes the SAIB formulation loose (less viscous) while CAB is supposed to make it more cohesive and less deformable. One would not have expected, therefore, that increasing IPM would have the same effect as increasing CAB.

Figure 3:
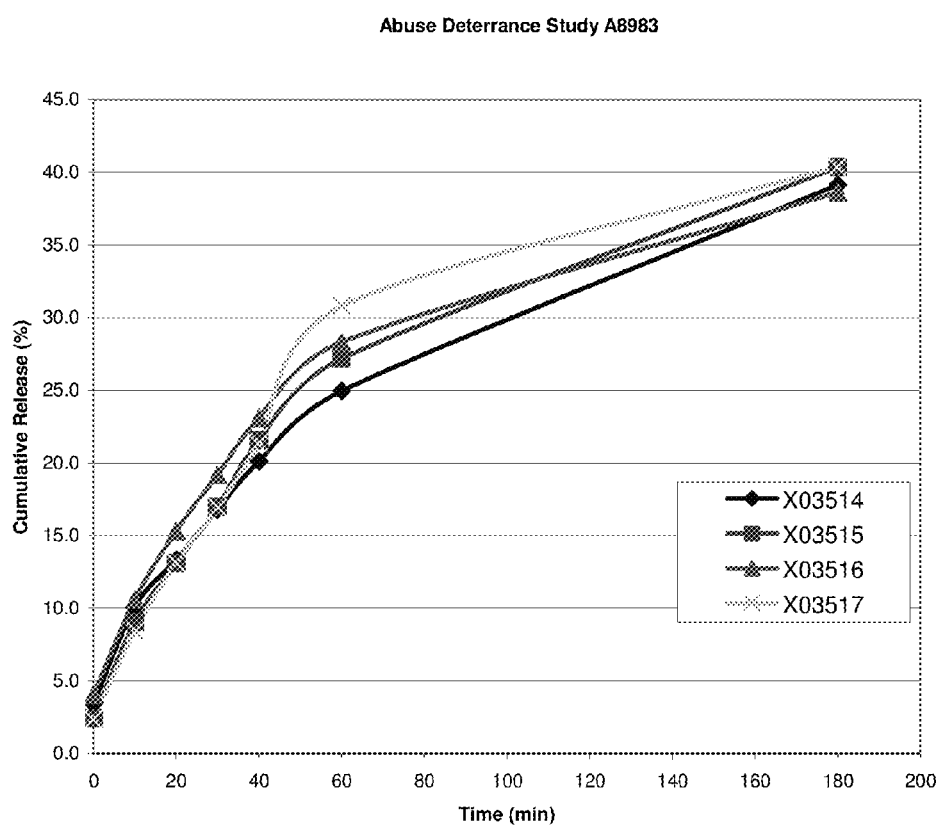

FIG. 3 shows cumulative percentage of drug extracted by alcoholic solution from various SAIB formulations vs. time (mins) for 4 formulations. Each formulation contains 12 mg/ml oxycodone. These formulations had IPM to CAB ratios ranging from 0.6 to 0.78 and calibrated content of ethyl lactate ranging from 27-29 wt. %. The figure demonstrates that at the end of 180 minute extraction experiment, the percentage extracted was approximately the same for all 4 formulations. However, at the end of the first 60 minutes, it was discovered that the percent extracted drug was higher with the formulations containing greater amounts of ethyl lactate. It was also found that extremely an small increment in ethyl lactate content led to a large increase in the extraction of drug.

Figure 4:
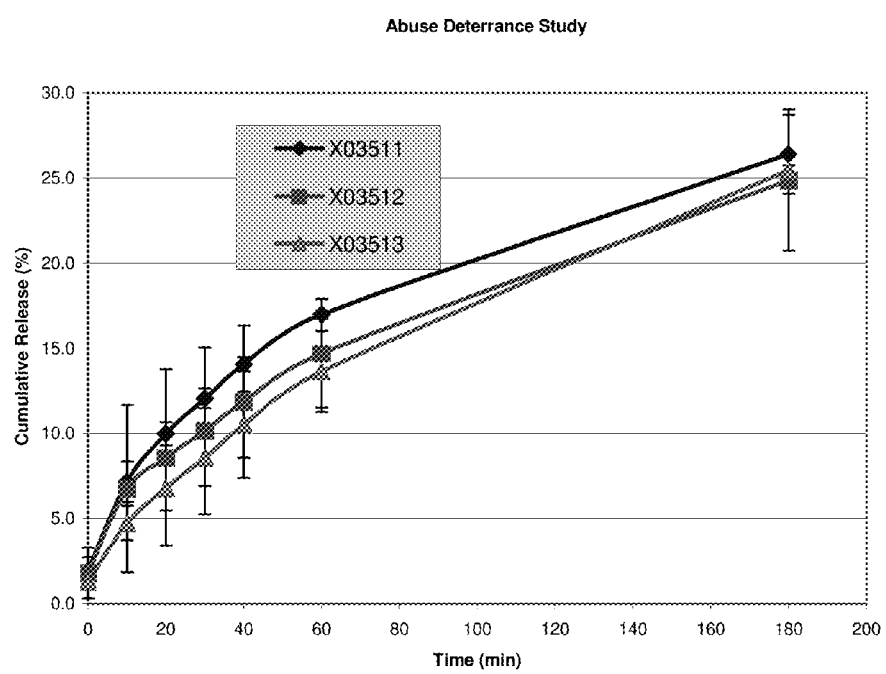

FIG. 4 Shows cumulative percentage of drug extracted by alcohol vs. time (mins) for 3 formulations. Each formulation contains 9 mg/ml oxycodone. This experiment demonstrated that ethyl lactate has greater influence on the drug extractability by alcohol than CAB by a factor of more than 2 fold. This was another unexpected discovery since it would have been reasonable to believe that CAB is a extremely effective matrix/network forming agent.

Figure 11:
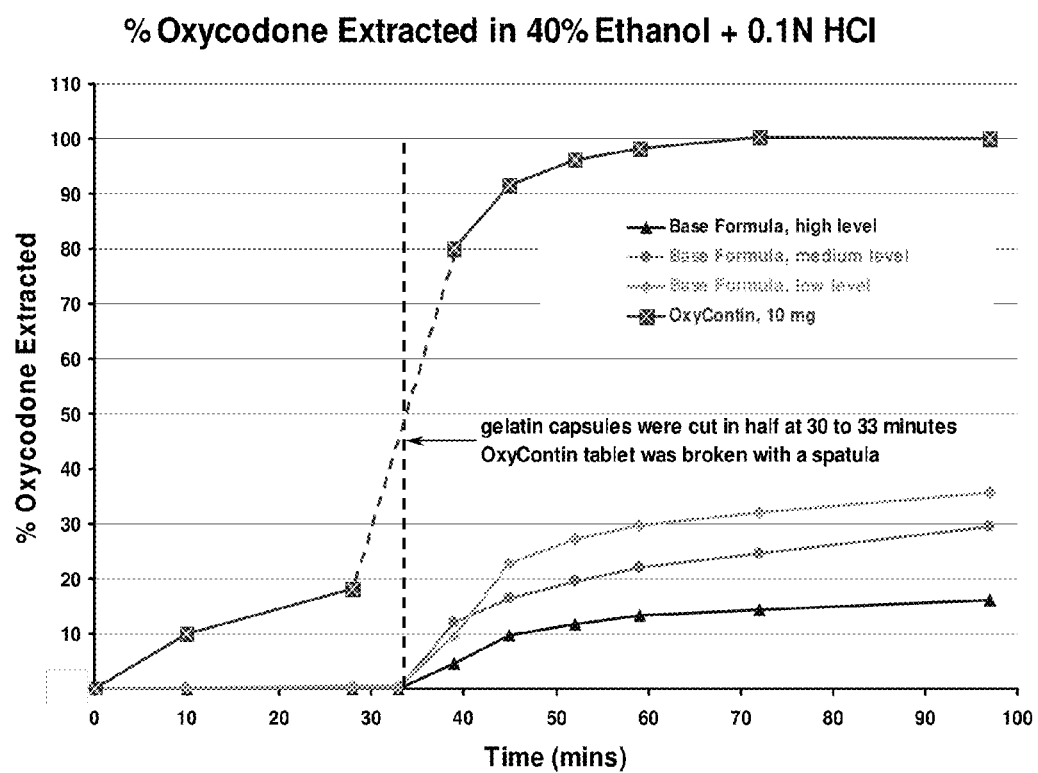

FIG. 11 shows the results of alcohol-extraction experiments. The graph displays a plots of % total oxycodone extracted into 40% ethanol+0.1N HCl vs. time. The control formulation used was a commercial 10 mg Oxycontin® tablet. The experimental formulations used in this experiment did not contain IPM and had the following ratios of SAIB:EL:CAB: "Base Formula, high level"=50:45:5; "Base Formula, medium level"=60.8:37:2.2; "Base Formula, low level"=50:48:2. In this experiment, at about 30 minutes, the gelatin capsule containing formulations disclosed herein was cut in half, and the tablet was crushed with a spatula. As can be seen, the OxyContin® tablet formulation rapidly releases 100% of drug after crushing. After about 60 minutes, all the drug is released. For the three SAIB formulations, however, the % drug released after 60 mins is only about 13%, 23% and 30% for the low, medium and high formulations, respectively. These results clearly demonstrate that the formulations of the invention have significantly improved abuse-deterrence characteristics when compared with the current Oxycontin® tablet formulation.

Extraction of Drug into Water

Another experiment was performed to determine the degree to which the formulation of the invention possessed abuse deterrent characteristics, specifically to determine the extractability of Oxycodone into water. Typically, a drug abuser may crush and grind an oxycodone tablet and dissolve it in water to extract the drug into aqueous solution for injecting. In the present experiment, the experimental dosage form was a SAIB-oxycodone gelcap with a formulation of SAIB:EL:IPM:CAB at a ratio of 67:26:3:4, contained in a soft gelatin capsule, and containing 9 mg of drug (oxycodone free base). The control dosage form used was a 9 mg Oxycontin® tablet. Each dosage form was crushed with a mortar and pestle and ground in 5 ml water. The resulting solution/suspension was then filtered through a 0.45 micron filter into a flask and diluted to 50 ml with water. Oxycodone concentration was then quantified by HPLC. The results were as follows: For the control (OxyContin® tablets), 100% of the oxycodone was extracted from the crushed tablet into water. For the experimental SAIB formulation, only about 21% of oxycodone extracted into water. This shows that the current formulation has considerable drug-abuse deterrence characteristics when compared with the Oxycontin® tablet, because the drug cannot be efficiently extracted into water.

Physical Treatment

Figure 8:
FIG. 8 is a representative photograph of a 100% SAIB formulation following exposure to temperature at −80° C. (−112° F.) for eight hours and crushing with a hammer. Note the controlled release matrix structure is preserved.
Figure 9:
FIG. 9 is a representative photograph of a formulation comprising SAIB+solvent, following exposure to temperature at −80° C. for eight hours and crushing with a hammer.
Figure 10:
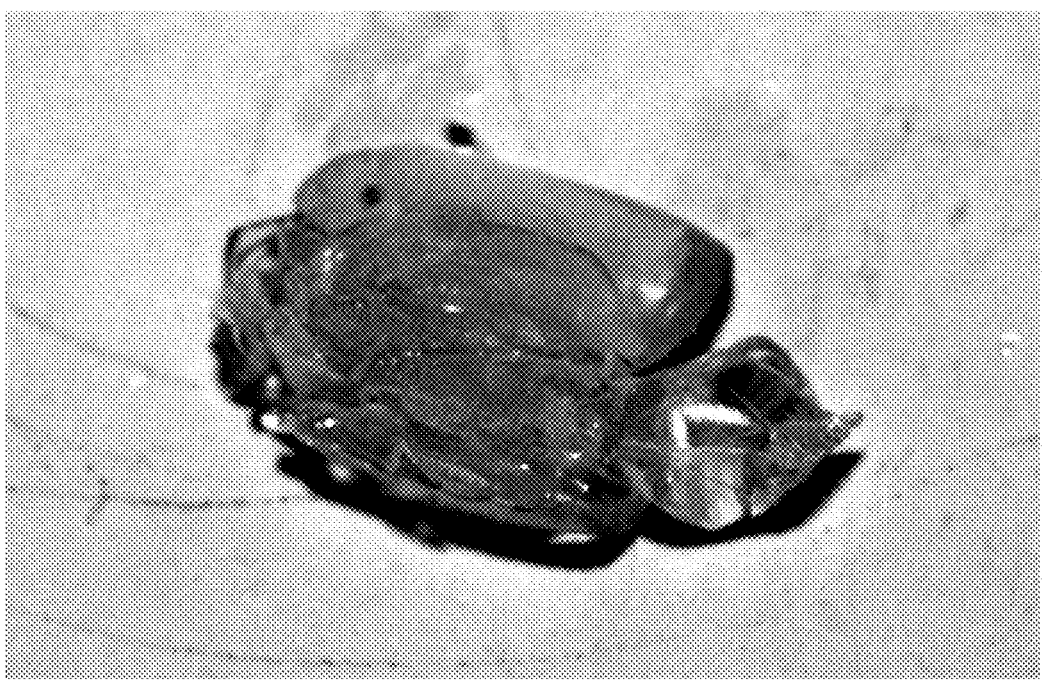
FIG. 10 is a representative photograph of a formulation of the invention (PTI-821, which is SAIB:EL:IPM:CAB at a ratio of 67:26:3:4) contained in a soft gelatin capsule, and containing 9 mg of drug) formulation following exposure to temperature at −80° C. for eight hours and crushing with a hammer.

Another potential method for drug abuse is to lower the temperature and mechanically crush a drug formulation so as to produce a powder which then can be inhaled or dissolved in a solution for injection. An experiment was performed to determine the characteristics of the current formulation, specifically with regard to lowering the temperature and crushing. In this procedure the formulation was placed in a laboratory freezer at −80° C. for eight hours, after which it was struck sharply with a hammer. One formulation comprised 100% SAIB, one formulation comprised SAIB plus a solvent (26% EL), and one formulation was a formulation of SAIB:EL:IPM:CAB at a ratio of 67:26:3:4 and oxycodone free base (see above). For the first formulation (100% SAIB) the results were as follows: Within about 45 seconds of being crushed, the fragments thawed and returned to the state of a high viscosity liquid. The controlled release matrix structure of the formulation was preserved. For the second formulation (SAIB+solvent): Within about 30 seconds after being crushed the formulation mass appeared highly viscous and sticky and did not fracture into discreet fragments. Again, the controlled release matrix structure was preserved. For the PTI-821 formulation: Within about 30 seconds after being crushed the formulation appeared highly viscous and tacky and did not fracture into fragments. Once again, the controlled release matrix structure was preserved. Consequently, attempted abuse by lowering temperature and crushing would not result in a readily abusable form of drug. See FIGS. 8-10.

Plasma Level Study

FIG. 5 is a graph from a dog PK study showing plasma concentration (ng/ml) vs. time (hr) for three SAIB soft gelcaps containing 9 mg oxycodone formulations (A, B and C) and Oxycontin® (A=SAIB:EL:CAB; B=SAIB:EL:CAB; C=SAIB:EL:CAB, CAB=CAB 171-15). A single gelcap containing about 0.75 g of each of oxycodone formulations was administered to a dog orally. Blood was drawn periodically over 12 hours and the plasma concentration of oxycodone was determined as a function of time.

Plasma vs. time profiles for three formulations A, B and C, were compared against that for Oxycontin®. The SAIB gelcap formulations and the Oxycontin® tablets each contained an identical amount of oxycodone free base (9 mg).

SAIB formulations A and C exhibited higher Cmax (maximum plasma concentration of drug) values than the Oxycontin® tablet formulation. The two SAIB formulations A and B had a significantly shorter Tmax (time to maximum plasma level) values compared with Oxycontin®. On the other hand, SAIB formulation B which has a highest viscosity of A, B and C, shows equivalent Cmax but longer Tmax values compared with the Oxycontin® control.

SAIB formulations A and C also gave greater AUC (area under the plasma drug concentration vs. time curve) values and bioavailability due to their unique rheological (flow) characteristics compared to Oxycontin® reference. It was discovered that optimum SAIB formulations, which manifest desirable pharmacokinetic profiles, must possess the following viscosity characteristics: the SAIB solution viscosity at 37° C. should be in the range from 1,000-30,000 cP. Further more the SAIB formulations following immersion in 37° C. water or aqueous buffer (pH 1-10) for 4-5 hours should optimally have the viscosity at 37° C. ranging from 3,000-50,000 cP.

Although a number of the examples provided above relate to compositions according to the invention containing oxycodone in amounts of approximately 10 mg per SAIB formulation gelcap, larger or smaller amounts of drug (e.g., 5 mg, 20 mg, 40 mg, 80 mg, 160 mg, and the like) can be incorporated into SAIB gelcaps according to the invention.

While the benefits of the invention have been described with respect to certain drugs, such as opioids, some or all of these benefits are obtained when the formulation of the invention is used with a wide variety of drugs, such as immunosuppressants, antioxidants, anesthetics, chemotherapeutic agents, steroids (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds, antipsychotics, and radiation absorbers, including UV-absorbers, chemotherapeutic agents, anti-nausea medication, and the like. Non-limiting examples of pharmacological materials or drugs suitable for use in the invention include anti-infectives such as nitrofurazone, sodium propionate, antibiotics, including penicillin, tetracycline, oxytetracycline, chlorotetracycline, bacitracin, nystatin, streptomycin, neomycin, polymyxin, gramicidin, chloramphenicol, erythromycin, and azithromycin; sulfonamides, including sulfacetamide, sulfamethizole, sulfamethazine, sulfadiazine, sulfamerazine, and sulfisoxazole, and anti-virals including idoxuridine; antiallergenics such as antazoline, methapyritene, chlorpheniramine, pyrilamine prophenpyridamine, hydrocortisone, cortisone, hydrocortisone acetate, dexamethasone, dexamethasone 21-phosphate, fluocinolone, triamcinolone, medrysone, prednisolone, prednisolone 21-sodium succinate, and prednisolone acetate; desensitizing agents such as ragweed pollen antigens, hay fever pollen antigens, dust antigen and milk antigen; vaccines such as smallpox, yellow fever, distemper, hog cholera, chicken pox, antivenom, scarlet fever, dyptheria toxoid, tetanus toxoid, pigeon pox, whooping cough, influenzae rabies, mumps, measles, poliomyelitic, and Newcastle disease; decongestants such as phenylephrine, naphazoline, and tetrahydrazoline; miotics and anticholinesterases such as pilocarpine, esperine salicylate, carbachol, diisopropyl fluorophosphate, phospholine iodide, and demecarium bromide; parasympatholytics such as atropine sulfate, cyclopentolate, homatropine, scopolamine, tropicamide, eucatropine, and hydroxyamphetamine; sympathomimetics such as epinephrine; sedatives and hypnotics such as pentobarbital sodium, phenobarbital, secobarbital sodium, codeine, (a-bromoisovaleryl) urea, carbromal; psychic energizers such as 3-(2-aminopropyl) indole acetate and 3-(2-aminobutyl) indole acetate; tranquilizers such as reserpine, chlorpromayline, and thiopropazate; androgenic steroids such as methyltestosterone and fluorymesterone; estrogens such as estrone, 17-.beta.-estradiol, ethinyl estradiol, and diethyl stilbestrol; progestational agents such as progesterone, megestrol, melengestrol, chlormadinone, ethisterone, norethynodrel, 19-norprogesterone, norethindrone, medroxyprogesterone and 17-.beta.-hydroxy-progesterone; humoral agents such as the prostaglandins, for example $PGE_1$, $PGE_2$ and $PGF_2$; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine, antihistamines such as diphenhydramine, dimenhydrinate, tripelennamine, perphenazine, and chlorphenazine; cardioactive agents such as dibenzhydroflume thiazide, flumethiazide, chlorothiazide, and aminotrate; nutritional agents such as vitamins, natural and synthetic bioactive peptides and proteins, including growth factors, cell adhesion factors, cytokines, and biological response modifiers.

The embodiments disclosed herein are exemplary only, and are not meant to limit the invention, which should be interpreted solely in light of the claims.

What is claimed is:

1. A method of providing pain relief to a subject in need thereof, comprising orally administering to the subject an effective amount of a composition comprising:
   an opioid selected from buprenorphine, butorphanol, hydrocodone, hydromorphone, levorphanol, meperidine, methadone, morphine, oxycodone, oxymorphone, and tramadol, or a pharmacologically effective salt thereof;
   sucrose acetate isobutyrate (SAIB);
   a cellulose acetate butyrate (CAB) having a number average molecular weight ranging from 66,000 Daltons to 83,000 Daltons; and
   a solvent.

2. The method of claim 1, wherein the opioid is present in an amount ranging from about 2 mg to about 250 mg.

3. The method of claim 1, wherein the opioid comprises hydrocodone, hydromorphone, levorphanol, morphine, oxymorphone, or oxycodone.

4. The method of claim 1, wherein the composition comprises from about 20 weight percent to about 90 weight percent of the SAIB.

5. The method of claim 1, wherein the CAB has a butyryl content ranging from about 17% to about 38%.

6. The method of claim 1, wherein the CAB has an acetyl content ranging from about 13% to about 30%.

7. The method of claim 1, wherein the CAB has a butyryl content ranging from about 17% to about 38% and an acetyl content ranging from about 13% to about 30%.

8. The method of claim 1, wherein the CAB has at least one feature selected from a butyryl content ranging from about 17% to about 38%, an acetyl content ranging from about 13% to about 30%, and a hydroxyl content ranging from about 0.8% to about 1.7%.

9. The method of claim 1, wherein the composition comprises from about 20 weight percent to about 50 weight percent of the solvent.

10. The method of claim 1, wherein the solvent comprises propylene carbonate, N-methylpyrrolidone (NMP), glycofurol, alpha-tocopherol, diethyl phthalate, or polyethylene glycol 400 (PEG 400).

11. The method of claim 1, wherein the solvent comprises triacetin or ethyl lactate.

12. The method of claim 1, wherein the composition further comprises a member selected from caprylic/capric triglyceride, isopropyl myristate (IPM), ethyl oleate, dimethyl phthalate, and benzyl benzoate.

13. The method of claim 1, wherein the composition is contained in a capsule.

14. The method of claim 13, wherein the capsule comprises gelatin or hydroxyl propylmethyl cellulose.

15. The method of claim 13, wherein the capsule comprises a hard capsule comprising gelatin or hydroxyl propylmethyl cellulose.

16. The method of claim 1, wherein the composition further comprises isopropyl myristate (IPM).

17. The method of claim 16, wherein the composition comprises from about 1 weight percent to about 75 weight percent of the IPM.

18. The method of claim 16, wherein the composition comprises:
   from about 20 weight percent to about 90 weight percent of the SAIB;
   from about 1 weight percent to about 8.6 weight percent of the CAB;
   from about 1 weight percent to about 75 weight percent of the IPM; and
   from about 20 weight percent to about 50 weight percent of the solvent.

19. The method of claim 18, wherein the composition comprises from about 3 weight percent to about 7.8 weight percent of the CAB.

20. The method of claim 18, wherein the composition comprises from 0.1 weight percent to 10 weight percent of the IPM.

21. The method of claim 18, wherein the composition comprises:
   from about 30 weight percent to about 70 weight percent of the SAIB; and
   from about 25 weight percent to about 48 weight percent of the solvent.

\* \* \* \* \*